(12) United States Patent
Schriver et al.

(10) Patent No.: US 12,205,715 B2
(45) Date of Patent: *Jan. 21, 2025

(54) SYSTEM, METHOD, AND COMPUTER PROGRAM PRODUCT FOR PREDICTIVE MAINTENANCE

(71) Applicant: Bayer Healthcare LLC, Whippany, NJ (US)

(72) Inventors: Ralph Schriver, Tarentum, PA (US); Arthur Uber, III, Pittsburgh, PA (US); Janele Archibald, Broomfield, CO (US); Matthew Brewer, Fairchance, PA (US); Amy Chaya, Strafford, PA (US); Christopher Fiorentini, Oglesby, IL (US); David Griffiths, Pittsburgh, PA (US); Jacob Hartmann, Shawnee, KS (US); Joseph Hulbert, Wexford, PA (US); Susan Michel, Gibsonia, PA (US); Janel Petrilli, Pittsburgh, PA (US); Michael Pogozelec, Oxford, FL (US); Barry Skirble, Allison Park, PA (US)

(73) Assignee: BAYER HEALTHCARE LLC, Whippany, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 17/581,648

(22) Filed: Jan. 21, 2022

(65) Prior Publication Data

US 2022/0148718 A1     May 12, 2022

Related U.S. Application Data

(62) Division of application No. 16/623,934, filed as application No. PCT/US2018/000265 on Aug. 18, 2018, now Pat. No. 11,232,862.

(Continued)

(51) Int. Cl.
    *G16H 40/40*     (2018.01)
    *G05B 23/02*     (2006.01)
    (Continued)

(52) U.S. Cl.
    CPC ........... *G16H 40/40* (2018.01); *G05B 23/024* (2013.01); *G05B 23/0283* (2013.01); *G06Q 10/20* (2013.01); *G16H 20/17* (2018.01)

(58) Field of Classification Search
    CPC ...... G16H 40/40; G16H 20/17; G05B 23/024; G05B 23/0283; G06Q 10/20
    See application file for complete search history.

(56) References Cited

U.S. PATENT DOCUMENTS

| | | |
|---|---|---|
| 3,977,391 A | 8/1976 | Fleischmann |
| 6,317,623 B1 | 11/2001 | Griffiths et al. |
| | (Continued) | |

FOREIGN PATENT DOCUMENTS

| | | | |
|---|---|---|---|
| CN | 114360703 A | * | 4/2022 |
| EP | 1563859 A1 | | 8/2005 |
| | (Continued) | | |

OTHER PUBLICATIONS

Nuclear Engineering and Design 273 (2014) 202-214; Authors: Y. Appalanaidu, Sayan Gupta.

(Continued)

*Primary Examiner* — Sheetal R Paulson
(74) *Attorney, Agent, or Firm* — James R. Stevenson; Aaron A. Mace

(57) ABSTRACT

A method, system, and computer program product for predictive maintenance. A method may include receiving operation data associated with one or more injection systems, wherein the operation data includes one or more operation parameters associated with one or more operations of the one or more injection systems: determining one or more (Continued)

prediction scores for the one or more injection systems based on the operation data, wherein the one or more prediction scores include one or more predictions of one or more operation failures or misuses for the one or more injection systems; and providing maintenance data associated with the one or more operation failures or misuses, wherein the maintenance data is based on the one or more prediction scores.

33 Claims, 5 Drawing Sheets

Related U.S. Application Data

(60) Provisional application No. 62/547,300, filed on Aug. 18, 2017.

(51) Int. Cl.
*G06Q 10/20* (2023.01)
*G16H 20/17* (2018.01)

(56) References Cited

U.S. PATENT DOCUMENTS

| | | | |
|---|---|---|---|
| 6,643,537 | B1 | 11/2003 | Zatezalo et al. |
| 7,094,216 | B2 | 8/2006 | Trombley, III et al. |
| 7,457,804 | B2 | 11/2008 | Uber, III et al. |
| 7,549,977 | B2 | 6/2009 | Schriver et al. |
| 7,553,294 | B2 | 6/2009 | Lazzaro et al. |
| 7,556,619 | B2 | 7/2009 | Spohn et al. |
| 7,563,249 | B2 | 7/2009 | Schriver et al. |
| 7,766,873 | B2 | 8/2010 | Moberg et al. |
| 7,775,966 | B2 | 8/2010 | Dlugos et al. |
| 7,996,381 | B2 | 8/2011 | Uber, III et al. |
| 8,147,464 | B2 | 4/2012 | Spohn et al. |
| 8,337,456 | B2 | 12/2012 | Schriver et al. |
| 8,521,716 | B2 | 8/2013 | Uber, III et al. |
| 8,540,698 | B2 | 9/2013 | Spohn et al. |
| 8,945,051 | B2 | 2/2015 | Schriver et al. |
| 9,173,995 | B1 | 11/2015 | Tucker et al. |
| 9,463,335 | B2 | 10/2016 | Griffith et al. |
| 10,124,110 | B2 | 11/2018 | Pedig et al. |
| 10,507,319 | B2 | 12/2019 | Haury et al. |
| 10,549,084 | B2 | 2/2020 | Sokolov et al. |
| 10,583,256 | B2 | 3/2020 | Berry et al. |
| 2002/0070157 | A1 | 6/2002 | Yamada |
| 2003/0216692 | A1 | 11/2003 | Fago et al. |
| 2004/0138920 | A1 | 7/2004 | Sawanaga et al. |
| 2009/0070342 | A1 | 3/2009 | Uber, III et al. |
| 2010/0189227 | A1 | 7/2010 | Mannar et al. |
| 2010/0305506 | A1 | 12/2010 | Fahrer |
| 2012/0110651 | A1 | 5/2012 | Van Biljon et al. |
| 2012/0209569 | A1 | 8/2012 | Becourt et al. |
| 2014/0249500 | A1 | 9/2014 | Estes |
| 2014/0266713 | A1* | 9/2014 | Sehgal .................. G16H 40/40 340/540 |
| 2015/0201912 | A1 | 7/2015 | Mercer et al. |
| 2015/0374901 | A1 | 12/2015 | Kohler |
| 2016/0034722 | A1 | 2/2016 | Joseph et al. |
| 2016/0213853 | A1* | 7/2016 | Despa ................. A61M 5/3155 |
| 2017/0182258 | A1* | 6/2017 | Michael ................ G16H 20/17 |
| 2018/0161496 | A1 | 6/2018 | Berry et al. |
| 2018/0240548 | A1 | 8/2018 | Spohn et al. |
| 2018/0286510 | A1* | 10/2018 | Kwan .................... G06Q 10/20 |
| 2019/0050375 | A1 | 2/2019 | Fitzgibbon et al. |
| 2020/0310900 | A1 | 10/2020 | Hipp et al. |

FOREIGN PATENT DOCUMENTS

| | | | |
|---|---|---|---|
| JP | 2010509984 | A | 4/2010 |
| JP | 2011516196 | A | 5/2011 |
| WO | 2008063429 | A2 | 5/2008 |
| WO | 2009125398 | A2 | 10/2009 |
| WO | 2013075127 | A1 | 5/2013 |
| WO | 2016112163 | A1 | 7/2016 |
| WO | 2017027724 | A1 | 2/2017 |
| WO | 2017040152 | A1 | 3/2017 |
| WO | 2018075386 | A1 | 4/2018 |
| WO | 2018144369 | A1 | 8/2018 |
| WO | 2019035986 | A1 | 2/2019 |
| WO | WO-2019032784 | A1 * | 2/2019 ............ A61M 5/168 |
| WO | 2019046261 | A1 | 3/2019 |
| WO | 2019046282 | A1 | 3/2019 |

OTHER PUBLICATIONS

Charles; M. Able et al, "A model for preemptive maintenance of medical linear accelerators-predictive maintenance", Radiation Oncology, 2016, vol. 11/ No. 36.

"From Conventional Injector to Smart Injector Brochure for EmpowerCTA Injector System", 2017.

"International Preliminary Report on Patentability from PCT Application No. PCT/US2018/000265", Feb. 27, 2020.

Mana; Sezdi., "Two Different Maintenance Strategies in the Hospital Environment: Preventive Maintenance for Older Technology Devices and Predictive Maintenance for Newer High-Tech Devices", Journal of Healthcare Engineering, Hindawi Plublishing, 2016, vol. 2016.

Patil Ravindra; et al, "Predictive Modeling for Corrective Maintenance of Imaging devices from Machine Logs", IEEE, 2017, 1676-1679.

"International Preliminary Report on Patentability from PCT Application No. PCT/US2020/061161", Jun. 2, 2022.

* cited by examiner

SYSTEM, METHOD, AND COMPUTER PROGRAM PRODUCT FOR PREDICTIVE MAINTENANCE

CROSS-REFERENCE TO RELATED APPLICATIONS

This application claims the benefit of U.S. Provisional Application No. 62/547,300, filed Aug. 18, 2017, the entire disclosure of which is hereby incorporated by reference in its entirety.

BACKGROUND OF THE INVENTION

1. Field of the Invention

This disclosure relates generally to systems, devices, products, apparatus, and methods that are used for predictive maintenance, and in one particular embodiment, to a system, product, and method for predictive maintenance of injection systems.

2. Technical Considerations

Availability (e.g., uptime for performing operations, proper functioning and/or performance of operations, non-failure of components, devices, functions, and/or operations, etc.) and proper use (e.g., by a user or operator, etc.) of an injection system, for example, as part of an imaging suite, can affect life-saving diagnosis and monitoring of medical treatment for a disease or medical condition of a patient. If an injection system (e.g., if one or more components or devices of an injection system, etc.) fails or is used improperly, imaging can be interrupted and/or a medical procedure and/or treatment for a patient may be delayed and/or improperly performed. Accordingly, there is a need in the art to improve availability and usage of injection systems (e.g., to reduce or prevent downtime, improper functioning, failure, and/or improper use by users or operators of injection systems, etc.).

SUMMARY OF THE INVENTION

Accordingly, provided are systems, devices, products, apparatus, and/or methods for a maintenance prediction system that improves availability and/or usage of injection systems by predicting operation failures and/or misuses for injection systems before the injection systems fail and/or are improperly used and by providing maintenance data associated with the predicted operation failures and/or misuses. For example, conventional injection systems have no mechanism for predicting operation failures and/or misuses before the injection systems (e.g., before one or more components or devices of the injection systems, before one or more operations of the injection systems, etc.) fail and/or are improperly used. In this way, conventional injection systems may not provide for: repairing, servicing, upgrading, and/or replacing (e.g., scheduling and/or performing a repair, service, upgrade, and/or replacement, etc.) of an injection system (e.g., one or more components or devices of an injection system, etc.) before the injection system fails and/or is misused; providing maintenance data (e.g., maintenance actions, training information, etc.) to a user or operator of the injection system that the user or operator can implement to reduce a risk (e.g., a probability, a likelihood, etc.) of failure and/or misuse of the injection system; providing maintenance data (e.g., information on correct components and/or devices (e.g., replacement parts, service tools, etc.) and/or operations (e.g., service records, error codes, service procedures, etc.)) to a service technician and/or a user or operator of an injection system for repairing, servicing, upgrading, and/or replacing the injection system; automatically ensuring regulatory compliance of an injection system before the injection system becomes incompliant with one or more regulations; service benchmarking of inventory systems; and/or the like.

According to a non-limiting embodiment or aspect, provided is a computer-implemented method for predictive maintenance, comprising: receiving, with a computer system comprising one or more processors, operation data associated with one or more injection systems, wherein the operation data includes one or more operation parameters associated with one or more operations of the one or more injection systems; determining, with the computer system, one or more prediction scores for the one or more injection systems based on the operation data, wherein the one or more prediction scores include one or more predictions of one or more operation failures or misuses for the one or more injection systems; and providing, with the computer system, maintenance data associated with the one or more operation failures or misuses, wherein the maintenance data is based on the one or more prediction scores.

According to a non-limiting embodiment or aspect, provided is a predictive maintenance system comprising: a computer system comprising one or more processors programmed or configured to: receive operation data associated with one or more injection systems, wherein the operation data includes one or more operation parameters associated with one or more operations of the one or more injection systems; determine one or more prediction scores for the one or more injection systems based on the operation data, wherein the one or more prediction scores include one or more predictions of one or more operation failures or misuses for the one or more injection systems; and provide maintenance data associated with the one or more operation failures or misuses, wherein the maintenance data is based on the one or more prediction scores.

According to a non-limiting embodiment or aspect, provided is a computer program product for predictive maintenance, the computer program product comprising at least one non-transitory computer-readable medium comprising one or more instructions that, when executed by at least one processor, cause the at least one processor to: receive operation data associated with one or more injection systems, wherein the operation data includes one or more operation parameters associated with one or more operations of the one or more injection systems; determine one or more prediction scores for the one or more injection systems based on the operation data, wherein the one or more prediction scores include one or more predictions of one or more operation failures or misuses for the one or more injection systems; and provide maintenance data associated with the one or more operation failures or misuses, wherein the maintenance data is based on the one or more prediction scores.

In some non-limiting embodiments or aspects, the maintenance data includes a prompt to a user to initiate at least one maintenance action associated with the one or more injection systems.

In some non-limiting embodiments or aspects, the at least one maintenance action includes at least one of the following: scheduling a service for the one or more injection systems, operating the one or more injection systems in a specific manner indicated by the maintenance data, or any combination thereof.

In some non-limiting embodiments or aspects, the maintenance data includes an instruction to the one or more injection systems that causes the one or more injection systems to automatically initiate at least one maintenance action.

In some non-limiting embodiments or aspects, the at least one maintenance action includes at least one of the following: scheduling a service for the one or more injection systems, performing a specific operation with the one or more injection systems, or any combination thereof.

In some non-limiting embodiments or aspects, the one or more operation parameters include a cleanliness rating associated with a cleanliness of the one or more injection systems.

In some non-limiting embodiments or aspects, the method further comprises: determining, with the computer system, the cleanliness rating based on at least one of the following: one or more images of the one or more injection systems, one or more force measurements of an injector motor of the one or more injection systems, or any combination thereof.

In some non-limiting embodiments or aspects, the one or more processors are further programmed or configured to: determine the cleanliness rating based on at least one of the following: one or more images of the one or more injection systems, one or more force measurements of an injector motor of the one or more injection systems, or any combination thereof.

In some non-limiting embodiments or aspects, the instructions further cause the at least one processor to: determine the cleanliness rating based on at least one of the following: one or more images of the one or more injection systems, one or more force measurements of an injector motor of the one or more injection systems, or any combination thereof.

In some non-limiting embodiments or aspects, the more operation failures or misuses for the one or more injection systems include at least one of the following: failure of an electrical component, failure of a software component, failure of a mechanical component, receiving, with the one or more injection systems, of user input from a user of the one or more injection systems that causes the one or more injection systems to operate contrary to one or more predefined operation thresholds, or any combination thereof.

Further non-limiting embodiments or aspects are set forth in the following numbered clauses:

Clause 1. A computer-implemented method for predictive maintenance, comprising: receiving, with a computer system comprising one or more processors, operation data associated with one or more injection systems, wherein the operation data includes one or more operation parameters associated with one or more operations of the one or more injection systems; determining, with the computer system, one or more prediction scores for the one or more injection systems based on the operation data, wherein the one or more prediction scores include one or more predictions of one or more operation failures or misuses for the one or more injection systems: and providing, with the computer system, maintenance data associated with the one or more operation failures or misuses, wherein the maintenance data is based on the one or more prediction scores.

Clause 2. The computer-implemented method of clause 1, wherein the maintenance data includes a prompt to a user to initiate at least one maintenance action associated with the one or more injection systems.

Clause 3. The computer-implemented method of any of clauses 1 and 2, wherein the at least one maintenance action includes at least one of the following: scheduling a service for the one or more injection systems, operating the one or more injection systems in a specific manner indicated by the maintenance data, or any combination thereof.

Clause 4. The computer-implemented method of any of clauses 1-3, wherein the maintenance data includes an instruction to the one or more injection systems that causes the one or more injection systems to automatically initiate at least one maintenance action.

Clause 5. The computer-implemented method of any of clauses 1-4, wherein the at least one maintenance action includes at least one of the following: scheduling a service for the one or more injection systems, performing a specific operation with the one or more injection systems, or any combination thereof.

Clause 6. The computer-implemented method of any of clauses 1-5, wherein the one or more operation parameters include a cleanliness rating associated with a cleanliness of the one or more injection systems, the method further comprising: determining, with the computer system, the cleanliness rating based on at least one of the following: one or more images of the one or more injection systems, one or more force measurements of an injector motor of the one or more injection systems, or any combination thereof.

Clause 7. The computer-implemented method of any of clauses 1-6, wherein the more operation failures or misuses for the one or more injection systems include at least one of the following: failure of an electrical component, failure of a software component, failure of a mechanical component, receiving, with the one or more injection systems, of user input from a user of the one or more injection systems that causes the one or more injection systems to operate contrary to one or more predefined operation thresholds, or any combination thereof.

Clause 8. A predictive maintenance system comprising: a computer system comprising one or more processors programmed or configured to: receive operation data associated with one or more injection systems, wherein the operation data includes one or more operation parameters associated with one or more operations of the one or more injection systems; determine one or more prediction scores for the one or more injection systems based on the operation data, wherein the one or more prediction scores include one or more predictions of one or more operation failures or misuses for the one or more injection systems; and provide maintenance data associated with the one or more operation failures or misuses, wherein the maintenance data is based on the one or more prediction scores.

Clause 9. The system of clause 8, wherein the maintenance data includes a prompt to a user to initiate at least one maintenance action associated with the one or more injection systems.

Clause 10. The system of any of clauses 8 and 9, wherein the at least one maintenance action includes at least one of the following: scheduling a service for the one or more injection systems, operating the one or more injection systems in a specific manner indicated by the maintenance data, or any combination thereof.

Clause 11. The system of any of clauses 8-10, wherein the maintenance data includes an instruction to the one or more injection systems that causes the one or more injection systems to automatically initiate at least one maintenance action.

Clause 12. The system of any of clauses 8-11, wherein the at least one maintenance action includes at least one of the following: scheduling a service for the one or more injection systems, performing a specific operation with the one or more injection systems, or any combination thereof.

Clause 13. The system of any of clauses 8-12, wherein the one or more operation parameters include a cleanliness rating associated with a cleanliness of the one or more injection systems, and wherein the one or more processors are further programmed or configured to: determine the cleanliness rating based on at least one of the following: one or more images of the one or more injection systems, one or more force measurements of an injector motor of the one or more injection systems, or any combination thereof.

Clause 14. The system of any of clauses 8-13, wherein the more operation failures or misuses for the one or more injection systems include at least one of the following: failure of an electrical component, failure of a software component, failure of a mechanical component, receiving, with the one or more injection systems, of user input from a user of the one or more injection systems that causes the one or more injection systems to operate contrary to one or more predefined operation thresholds, or any combination thereof.

Clause 15. A computer program product for predictive maintenance, the computer program product comprising at least one non-transitory computer-readable medium comprising one or more instructions that, when executed by at least one processor, cause the at least one processor to: receive operation data associated with one or more injection systems, wherein the operation data includes one or more operation parameters associated with one or more operations of the one or more injection systems; determine one or more prediction scores for the one or more injection systems based on the operation data, wherein the one or more prediction scores include one or more predictions of one or more operation failures or misuses for the one or more injection systems; and provide maintenance data associated with the one or more operation failures or misuses, wherein the maintenance data is based on the one or more prediction scores.

Clause 16. The computer program product of clause 15, wherein the maintenance data includes a prompt to a user to initiate at least one maintenance action associated with the one or more injection systems.

Clause 17. The computer program product of any of clauses 15 and 16, wherein the at least one maintenance action includes at least one of the following: scheduling a service for the one or more injection systems, operating the one or more injection systems in a specific manner indicated by the maintenance data, or any combination thereof.

Clause 18. The computer program product of any of clauses 15-17, wherein the maintenance data includes an instruction to the one or more injection systems that causes the one or more injection systems to automatically initiate at least one maintenance action.

Clause 19. The computer program product of any of clauses 15-18, wherein the at least one maintenance action includes at least one of the following: scheduling a service for the one or more injection systems, performing a specific operation with the one or more injection systems, or any combination thereof.

Clause 20. The computer program product of any of clauses 15-19, wherein the one or more operation parameters include a cleanliness rating associated with a cleanliness of the one or more injection systems, and wherein the instructions further cause the at least one processor to: determine the cleanliness rating based on at least one of the following: one or more images of the one or more injection systems, one or more force measurements of an injector motor of the one or more injection systems, or any combination thereof.

Clause 21. The computer program product of any of clauses 15-20, wherein the more operation failures or misuses for the one or more injection systems include at least one of the following: failure of an electrical component, failure of a software component, failure of a mechanical component, receiving, with the one or more injection systems, of user input from a user of the one or more injection systems that causes the one or more injection systems to operate contrary to one or more predefined operation thresholds, or any combination thereof.

These and other features and characteristics of the present invention, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and the claims, the singular form of "a," "an," and "the" include plural referents unless the context clearly dictates otherwise.

BRIEF DESCRIPTION OF THE DRAWINGS

Additional advantages and details of the invention are explained in greater detail below with reference to the exemplary embodiments or aspects that are illustrated in the accompanying schematic figures, in which.

DETAILED DESCRIPTION OF THE INVENTION

Figure 1A:
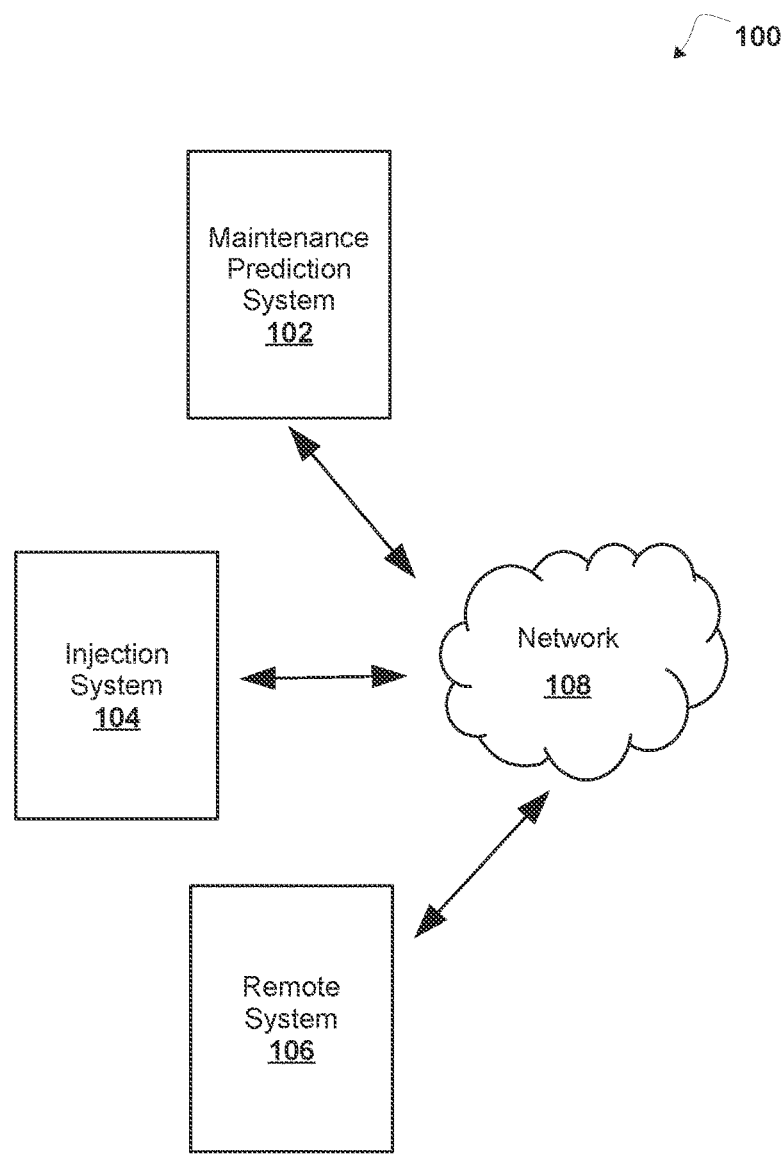
FIG. 1A is a diagram of a non-limiting embodiment or aspect of an environment in which systems, devices, products, apparatus, and/or methods, described herein, may be implemented according to the principles of the present invention.

For purposes of the description hereinafter, the terms "end," "upper," "lower," "right," "left," "vertical," "horizontal," "top," "bottom," "lateral," "longitudinal," and derivatives thereof shall relate to the invention as it is oriented in the drawing figures. However, it is to be understood that the invention may assume various alternative variations and step sequences, except where expressly specified to the contrary. It is also to be understood that the specific devices and processes illustrated in the attached drawings, and described in the following specification, are simply exemplary embodiments or aspects of the invention. Hence, specific dimensions and other physical characteristics related to the embodiments or aspects of the embodiments or aspects disclosed herein are not to be considered as limiting unless otherwise indicated.

No aspect, component, element, structure, act, step, function, instruction, and/or the like used herein should be construed as critical or essential unless explicitly described as such. Also, as used herein, the articles "a" and "an" are intended to include one or more items, and may be used interchangeably with "one or more" and "at least one." Furthermore, as used herein, the term "set" is intended to include one or more items (e.g., related items, unrelated items, a combination of related and unrelated items, etc.) and may be used interchangeably with "one or more" or "at least one," Where only one item is intended, the term "one" or similar language is used. Also, as used herein, the terms "has," "have," "having," or the like are intended to be open-ended terms. Further, the phrase "based on" is intended to mean "based at least partially on" unless explicitly stated otherwise.

As used herein, the terms "communication" and "communicate" may refer to the reception, receipt, transmission, transfer, provision, and/or the like of information (e.g., data, signals, messages, instructions, commands, and/or the like). For one unit (e.g., a device, a system, a component of a device or system, combinations thereof, and/or the like) to be in communication with another unit means that the one unit is able to directly or indirectly receive information from and/or transmit information to the other unit. This may refer to a direct or indirect connection that is wired and/or wireless in nature. Additionally, two units may be in communication with each other even though the information transmitted may be modified, processed, relayed, and/or routed between the first and second unit. For example, a first unit may be in communication with a second unit even though the first unit passively receives information and does not actively transmit information to the second unit. As another example, a first unit may be in communication with a second unit if at least one intermediary unit (e.g., a third unit located between the first unit and the second unit) processes information received from the first unit and communicates the processed information to the second unit. In some non-limiting embodiments or aspects, a message may refer to a network packet (e.g., a data packet and/or the like) that includes data. It will be appreciated that numerous other arrangements are possible. It will be appreciated that numerous other arrangements are possible.

As used herein, the term "server" may refer to one or more computing devices, such as processors, storage devices, and/or similar computer components that communicate with client devices and/or other computing devices over a network, such as the Internet or private networks, and, in some examples, facilitate communication among other servers and/or client devices. It will be appreciated that various other arrangements are possible. As used herein, the term "system" may refer to one or more computing devices or combinations of computing devices such as, but not limited to, processors, servers, client devices, software applications, and/or other like components. In addition, reference to "a server" or "a processor," as used herein, may refer to a previously-recited server and/or processor that is recited as performing a previous step or function, a different server and/or processor, and/or a combination of servers and/or processors. For example, as used in the specification and the claims, a first server and/or a first processor that is recited as performing a first step or function may refer to the same or different server and/or a processor recited as performing a second step or function.

Non-limiting embodiments or aspects of the present invention are directed to systems, devices, products, apparatus, and/or methods for a maintenance prediction system that improves availability and/or usage of injection systems by predicting operation failures and/or misuses for injection systems before the injection systems fail and/or are improperly used and by providing maintenance data associated with the predicted operation failures and/or misuses.

In this way, embodiments or aspects of the present invention provide for: (I) repairing, servicing, upgrading, and/or replacing (e.g., scheduling and/or performing a repair, service, upgrade, and/or replacement, etc.) of an injection system (e.g., one or more components or devices of an injection system, etc.) before the injection system (e.g., before one or more components or devices of the injection system, before one or more operations of the injection system, etc.) fails and/or is misused, which can (a) decrease or prevent downtime of the injection system, (b) increase a lifetime of the injection system (e.g., decrease a time to a failure requiring replacement of the injection system, etc.), (c) increase a number and/or a likelihood of successful procedures and/or treatments for patients, (d) increase efficiency in scheduling and/or performance of repairs, services, upgrades and/or replacements (e.g., automatically schedule and/or perform a repair, service, upgrade, and/or replacement with an injection system, automatically provide a prompt to a user to schedule and/or perform a repair, service, upgrade, and/or replacement at an injection system, etc.), or the like; (II) providing maintenance data (e.g., maintenance actions, training information, etc.) to a user or operator of the injection system that the user or operator can implement to reduce a risk (e.g., a probability, a likelihood, etc.) of failure and/or misuse of the injection system, which can (a) decrease or prevent continued misuse of the injection system, (b) increase image quality and/or patient care (e.g., decrease an occurrence of repeat injections and/or scans, etc.), (c) decrease contrast waste, and/or the like; (III) providing maintenance data (e.g., information on components and/or devices (e.g., replacement parts, service tools, etc.) and/or operations (e.g., service records, error codes, service procedures, etc.)) to a service technician and/or a user or operator of an injection system for repairing, servicing, upgrading, and/or replacing the injection system, which can (a) ensure that a service technician has the correct parts, tools, and/or information for a particular repair, service, upgrade, and/or replacement, (b) improve efficiency in scheduling of multiple repairs, services, upgrades and/or replacements, and/or the like; (IV) automatically ensuring regulatory compliance of an injection system before the injection system becomes incompliant with one or more regulations, which can (a) ensure calibration settings of the injection system, (b) reduce patient infections, (c) improve cleanliness of the injection system, and/or the like; (V) service benchmarking of inventory systems, which can (a) provide information for warranty prediction, service inventory planning, service resource planning, etc. that a user or customer can use to improve a knowledge base for preventative maintenance, (b) define use cases for future products, (c) improve training focus areas, and/or the like; and/or the like.

Referring now to FIG. 1A, FIG. 1A is a diagram of an example environment 100 in which devices, systems, and/or methods, described herein, may be implemented. As shown in FIG. 1A, environment 100 includes maintenance prediction system 102, injection system 104, remote system 106, and/or network 108. Maintenance prediction system 102, injection system 104, and/or remote system 106 may interconnect (e.g., establish a connection to communicate) via wired connections, wireless connections, or a combination of wired and wireless connections.

In some non-limiting embodiments or aspects, maintenance prediction system 102 includes one or more devices capable of receiving data and/or information (e.g., operation data, maintenance data, etc.) from injection system 104 and/or remote system 106 via network 108 and/or communicating data and/or information (e.g., operation data, maintenance data, etc.) to injection system 104 and/or remote system 106 via network 108. For example, maintenance prediction system 102 can include a computing device, such as one or more computers, portable computers (e.g., tablet computers), mobile devices (e.g., cellular phones, smartphones, wearable devices, such as watches, glasses, lenses, and/or clothing, PDAs, and/or the like), a server (e.g., a transaction processing server), a group of servers, and/or other like devices. In some non-limiting embodiments or aspects, maintenance prediction system 102 is in communication with a data storage device, which may be local or remote to maintenance prediction system 102. In some non-limiting embodiments or aspects, maintenance prediction system 102 is capable of receiving data and/or information from, storing data and/or information in, communicating data and/or information to, or searching data and/or information stored in the data storage device (e.g., operation data, maintenance data, etc.). In some non-limiting embodiments or aspects, maintenance prediction system 102 may be implemented within injection system 104 and/or remote system 106.

In some non-limiting embodiments or aspects, injection system 104 includes one or more devices capable of receiving data and/or information (e.g., operation data, maintenance data, etc.) from maintenance prediction system 102 and/or remote system 106 via network 108 and/or communicating data and/or information (e.g., operation data, maintenance data, etc.) to maintenance prediction system 102 and/or remote system 106 via network 108. For example, injection system 104 can include a computing device, such as a one or more computers, portable computers (e.g., tablet computers), mobile devices (e.g., cellular phones, smartphones, wearable devices, such as watches, glasses, lenses, and/or clothing, PDAs, and/or the like), a server (e.g., a transaction processing server), a group of servers, and/or other like devices. In some non-limiting embodiments or aspects, injection system 104 includes one or more devices (e.g., one or more sensors (e.g., a flow rate sensor, a temperature sensor, an accelerometer, a vibration monitoring sensor, a strain gauge, a motor current sensor, an optical sensor (e.g., a barcode scanner, etc.), an image sensor (e.g., a digital camera, etc.), one or more input components, one or more communication interfaces, etc.)) capable of receiving, determining, measuring, and/or sensing operation data associated with injection system 104. For example, operation data can include one or more operation parameters associated with one or more operations of injection system 104, and injection system 104 is capable of receiving, determining, measuring, and/or sensing the one or more operation parameters. In some non-limiting embodiments or aspects, injection system 104 is in communication with a data storage device, which may be local or remote to injection system 104. In some non-limiting embodiments or aspects, injection system 104 is capable of receiving data and/or information from, storing data and/or information in, communicating data and/or information to, or searching data and/or information stored in the data storage device (e.g., operation data, maintenance data, etc.).

In some non-limiting embodiment or aspects, injection system 104 includes a plurality of injection systems 104. For example, the plurality of injection systems 104 can be capable of receiving data and/or information (e.g., operation data, maintenance data, etc.) from maintenance prediction system 102, remote system 106, and/or each other via network 108 and/or communicating data and/or information (e.g., operation data, maintenance data, etc.) to maintenance prediction system 102, remote system 106, and/or each other via network 108. In some non-limiting embodiments or aspects, one or more injection systems of the plurality of injection systems 104 can be different from one or more other injection systems of the plurality of injection systems 104 (e.g., different types of injection systems, such as, injection systems from different manufacturers, different models of injection systems, different versions of a same model of injection system, injection systems for different types of injections (e.g., CT-based injections, MRI-based injections, etc.), and/or the like). In some non-limiting embodiments or aspects, one or more injection systems of the plurality of injection systems 104 can be the same as one or more other injection systems of the plurality of injection systems 104 (e.g., a same type of injection system, such as, injection systems from the same manufacturer, same models of injection system, same versions of a same model of injection system, injection systems for the same type of injection (e.g., CT-based injections, MRI-based injections, etc.), and/or the like). In some non-limiting embodiments or aspects, one or more injection systems of the plurality of injection systems 104 can be remote from one or more other injection systems of the plurality of injection systems 104 (e.g., separate injection systems at a same location, separate injection systems at a same imaging site, separate injection systems at different remote locations, separate injection systems at different imaging sites, etc,).

In some non-limiting embodiments or aspects, injection system 104 is configured to inject, deliver, or administer contrast fluid including a contrast agent to a patient, and in some non-limiting embodiments or aspects, injection system 104 is further configured to inject or administer saline or other fluid to a patient before, during, or after administration of contrast fluid. For example, injection system 104 can inject one or more prescribed dosages of contrast fluid directly into a patient's blood stream via a hypodermic needle and syringe. In some non-limiting embodiments or aspects, injection system 104 is configured to continually administer saline to a patient through a peripheral IV line (PIV) and catheter and one or more prescribed dosages of contrast fluid may be introduced into the PIV and administered via the catheter to the patient. In some non-limiting embodiments or aspects, injection system 104 is configured to inject a dose of contrast fluid followed by administration of a particular volume of saline.

In some non-limiting embodiments or aspects, injection system 104 is configured to administer a single contrast agent. In some non-limiting embodiments or aspects, injection system 104 is configured to deliver two or more different contrast agents. In implementations in which injection system 104 is configured to deliver multiple contrast agents, the injection system may allow the operator to switch configurations depending on the intended procedure. An amount of each contrast agent delivered by injection system 104 may vary based on an injection protocol being used. For example, specific injection protocols can be used to achieve desired blood, plasma, and/or tissue levels of contrast agent. A physician or other qualified medical personnel (and/or injection system 104) can determine an appropriate injection protocol according to which a contrast agent is to be delivered to a particular patient using metrics regarding the patient (e.g., age, weight, height, body mass index (BMI), cardiac output, a type of procedure to be performed, etc.). Injection system 104 may be configured to inject two or more contrast agents either individually, sequentially, or simultaneously. As such, in some non-limiting embodiments or aspects, injection system 104 can include two or more reservoirs, such as vials or syringes capable of holding a radiopharmaceutical prior to administration. Injection system 104 may further include additional medical fluid reservoirs capable of holding, for example, saline, other drugs, or other fluids.

In some non-limiting embodiments or aspects, injection system 104 includes one or more exemplary injection systems, fluid delivery systems, and/or injectors that are disclosed in: U.S. patent application Ser. No. 09/267,238, filed on Mar. 12, 1999, issued as U.S. Pat. No. 6,317,623; U.S. patent application Ser. No. 09/715,330, filed on Nov. 17, 2000, issued as U.S. Pat. No. 6,643,537; U.S. patent application Ser. No. 09/982,518, filed on Oct. 18, 2001, issued as U.S. Pat. No. 7,094,216; U.S. patent application Ser. No. 10/326,582, filed Dec. 20, 2002, issued as U.S. Pat. No. 7,549,977; U.S. patent application Ser. No. 10/825,866, filed on Apr. 16, 2004, issued as U.S. Pat. No. 7,556,619; U.S. patent application Ser. No. 12/437,011, filed May 7, 2009, issued as U.S. Pat. No. 8,337,456; U.S. patent application Ser. No. 12/476,513, filed Jun. 2, 2009, issued as U.S. Pat. No. 8,147,464; U.S. patent application Ser. No. 11/004,670, filed on Dec. 3, 2004, issued as U.S. Pat. No. 8,540,698; U.S. patent application Ser. No. 14/826,602, filed Aug. 14, 2015, issued as U.S. Pat. No. 9,463,335; International Patent Application Publication No. WO2017/027724A1, published Feb. 16, 2017, which was filed as International Application No. PCT/US2016/046587 on Aug. 11, 2016; and International Patent Application Publication No. WO2017/040152A1, published Mar. 9, 2017, which was filed as International Application No. PCT/US2016/048441 on Aug. 24, 2016, the disclosures of each of which are incorporated herein by reference in their entireties. In some non-limiting embodiments or aspects, injection system 104 includes the MEDRAD® Stellant CT Injection System with Certegra® Workstation provided by Bayer and/or the MEDRAD® MRXperion MR Injection System with the Radimetrics™ Enterprise Platform also provided by Bayer.

In some non-limiting embodiments or aspects, injection system 104 includes one or more flow rate sensors for directly measuring a flow rate and/or a volume of a fluid flow. For example, and referring to FIG. 1B, injection system 104 can include injector 120 configured to provide one or more fluids from one or more fluid sources (e.g., Fluid 1, Fluid 2, Fluid N, etc.) to flow tube 122 for delivery to medical device 128 (e.g., a catheter, etc.) according to an injection protocol (e.g., according to one or more injection parameters, etc.). As an example, injection system 104 can include flow rate sensor 124 (e.g., an ultrasonic mass flow rate sensor, such as manufactured by Transonic Systems, Inc., etc.) configured to measure a flow rate and/or a volume of a fluid flow. In such an example, flow rate sensor 124 can be configured to directly measure a flow rate of fluid flowing in flow tube 122 and/or a volume of the fluid flowing in flow tube 122 (e.g., a total volume delivered for an injection, etc.). Flow rate sensor 124 can measure the flow rate and/or volume of a fluid flow in flow tube 122, which is controlled and/or provided by injector 120 (e.g., a pump powered by a motor, etc.), such as a positive displacement pump, a non-positive displacement pump, a semi-positive displacement pump, a reciprocating pump, a piston pump, a vane pump, a flexible member pump, a lobe pump, a gear pump, a circumferential piston pump, a screw pump, a centrifugal pump, a turbine pump, an impeller pump, and/or the like. For example, flow rate sensor 124 can be attached to or mounted on (e.g., via a clip, an adhesive, etc.) an exterior surface of flow tube 122.

Figure 1B:
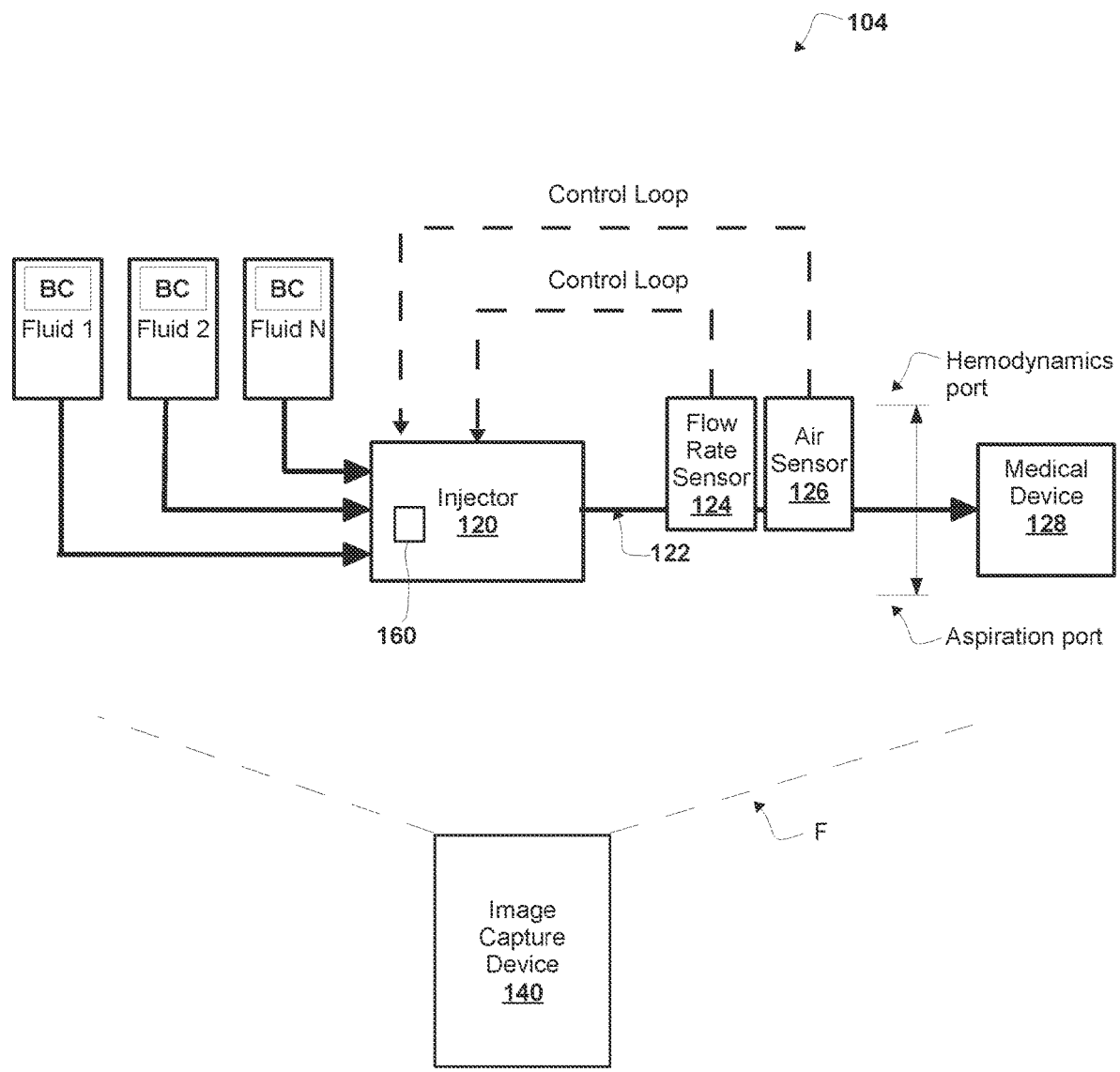
FIG. 1B is a diagram of a non-limiting embodiment or aspect of an injection system shown in FIG. 1A.

Still referring to FIG. 1B, in some non-limiting embodiments or aspects, flow rate sensor 124 provides a real-time feedback signal via a feedback control loop between flow rate sensor 124 and injector 120. For example, the real-time feedback signal may include a real-time measurement of the flow rate and/or volume of the fluid flow in flow tube 122. As an example, injector 120 can be programmed or configured to control the injection protocol (e.g., stop the injection, adjust injection control parameters, control fluid delivery to flow tube 122 from one or more fluid sources, etc.) based on the real-time feedback signal from flow rate sensor 124. In some non-limiting embodiments or aspects, injection system 104 (e.g., flow rate sensor 124, etc.) can be tuned or calibrated (e.g., include one or more operation parameters, etc.) for more accurate measurement of flow rate and/or volume of a fluid in a particular flow tube 122 (e.g., a particular disposable tubing set, etc.).

In some non-limiting embodiments or aspects, injection system 104 includes air sensor 126 configured to detect air or gas in a fluid flow. For example, air sensor 126 can be configured to directly measure an amount of air or gas in the fluid flowing in flow tube 122. In some non-limiting embodiments or aspects, air sensor 126 provides a real-time feedback signal via a feedback control loop between air sensor 126 and injector 120. For example, the real-time feedback signal may include a real-time measurement of the amount of gas in the fluid flowing in flow tube 122, As an example, injector 120 can be programmed or configured to control the injection protocol (e.g., adjust injection control parameters, control fluid delivery to flow tube 122, etc.) based on the real-time feedback signal from air sensor 126.

Although shown in FIG. 1B with respect to a single injector 120 (e.g., a single pump) controlling fluid delivery to a single flow tube 122 from multiple fluid sources 1, 2, . . . N, etc., with a single flow rate sensor 124 (and/or a single air sensor 126) providing a single real-time feedback signal to the single injector 120, non-limiting embodiments or aspects are not limited thereto, and injection system 104 may include a respective injector 120 (and/or one or more respective control valves, etc.) controlling fluid delivery to a respective flow tube 122 for each respective fluid source 1, 2, . . . N, etc., with a respective flow rate sensor 124 (and/or a respective air sensor 126) providing a respective real-time feedback signal to the respective injector 120. For example, each of the respective flow tubes 122 can be combined after the respective flow rate sensors 124 to deliver a combined fluid flow from each respective fluid source 1, 2, . . . N to medical device 128.

In some non-limiting embodiments or aspects, injection system 104 includes one or more sensors for measuring one or more operation parameters associated with a cleanliness of injection system 104. For example, dirt and/or fluids (e.g., contrast agent, etc.), can be unwantedly transferred via hands of a user or an operator and/or one or more drips or leaks to one or more components or devices of injection system 104. As an example, and referring to FIG. 1C, injector 120 can be enclosed within a housing 150 and include one or more ports 152 (e.g., syringe ports, etc.) for connecting to the proximal ends of one or more fluid sources 1, 2, . . . N (e.g., syringes 154 including Fluid 1, Fluid 2, etc,), and to connect plungers 156 to respective piston elements. The syringe ports 152 are generally located on one end of the housing 150, as shown, for example, in FIG. 1C.

In some non-limiting embodiments or aspects, a syringe 154 can include at least one bar code (BC), including information about the syringe dimensions, volume, pressure tolerances, and/or information about the fluid contained in the syringe 154. The at least one bar code (BC) can be read by an optical sensor 158, positioned on or recessed in the end of the housing 150 or within at least a portion of the inner surface of the at least one syringe port 154 of injector 120.

In some non-limiting embodiments or aspects, injection system 104 determines a cleanliness rating of injection system 104 and/or optical sensor 158 based on one or more scans of the at least one bar code (BC) by optical sensor 158. For example, injection system 104 can determine a numerical cleanliness rating based on a number of scans performed before a successful scan of the at least one bar code (BC) (e.g., more scans performed before a successful scan may indicate a lower cleanliness rating, decrement a cleanliness rating, etc.) and/or based on a percentage of a field of view of optical sensor 158 that is obscured (e.g., a higher obscured percentage of the field of view may indicate a lower cleanliness rating, decrease by the obscured percentage the cleanliness rating, etc.). In some non-limiting embodiments or aspects, injection system 104 can determine, in response to a maintenance action indicating that optical sensor 158 has been cleaned, a wear rating of injection system 104 and/or optical sensor 158. For example, injection system 104 can determine that a cause of the cleanliness rating is a more permanent operation failure (e.g., a scratch on a lens of optical sensor 158, etc.) than a less permanent operation failure (e.g., dirt or fluid on the lens of optical sensor 158, etc.) that can be repaired or removed by the cleaning action.

Figure 1C:
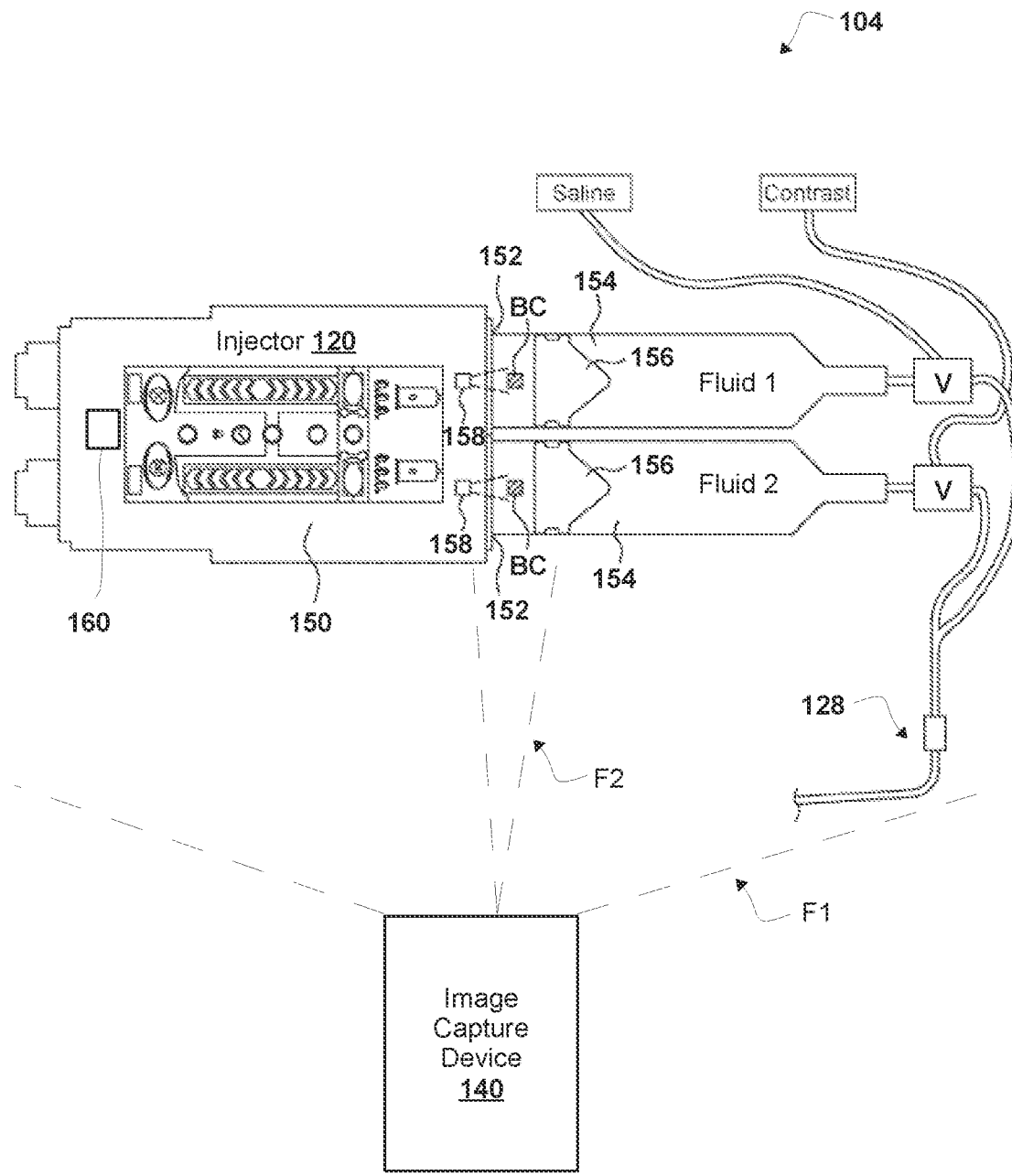
FIG. 1C is a diagram of a non-limiting embodiment or aspect of an injection system shown in FIG. 1A.

In some non-limiting embodiments or aspects, and referring to FIGS. 1B and 1C, injection system 104 can include an image capture device 140, such as a digital camera and/or the like, positioned to have a field of view that includes one or more components or devices of injection system 104 for capturing one or more images of the one or more components or devices of injection system 104. For example, and referring to FIG. 1B, injection system 104 can include image capture device 140 positioned to have a field of view (F) that includes each respective fluid source 1, 2, . . . . N, injector 120, flow tube 122, and/or medical device 128. As an example, and referring to FIG. 1C, injection system 104 can include image capture device 140 positioned to have a first field of view (F1) that includes each of housing 150, syringes 154, and/or medical device 128 and/or a second field of view (F2) that includes one or more specific components or component connections of injection system 104 (e.g., ports 152, a connection between ports 152 and syringes 154, etc.). In such examples, an image or images of the field of view can be obtained by image capture device 140, and injection system 104 can analyze the obtained image or images using image processing techniques, such as pattern recognition algorithms and/or the like, to identify a percentage of injection system 104 (or one or more components thereof) that is covered in unwanted contaminants (e.g., dirt, spilled contrast, etc.) and/or to identify a leak or a crack in one or more components or component connections of injection system 104. As an example, injection system 104 can use Insight Explorer imaging processing software from Cognex Corporation of Natick, MA, and image capture device 140 may be a DataMan 100 camera also from Cognex Corporation, to identify the percentage of injection system 104 that is covered in unwanted contaminants and/or to identify a leak or a crack in the one or more components or component connections of injection system 104. In such an example, injection system 104 can compare features of current images to training images or previous images to identify new or increased contaminant coverage and/or a leak or a crack in the one or more components or component connections of injection system 104.

In some non-limiting embodiments or aspects, image capture device 140 can be further configured to read at least one bar code (BC). For example, and referring again to FIG. 1B, fluid source 1, 2, . . . N can include at least one bar code (BC), including information about the fluid source dimensions, volume, pressure tolerances, and/or information about the fluid contained in the fluid source 1, 2, . . . N. The at least one bar code (BC) can be read by image capture device 140, for example, before, during, and/or after connecting the fluid source 1, 2, . . . N to injector 120. In such an example, injection system 104 can determine a numerical cleanliness rating based on a number of scans performed before a successful scan of the at least one bar code (BC) (e.g., more scans performed before a successful scan may indicate a lower cleanliness rating, decrement a cleanliness rating, etc.) and/or based on a percentage of a field of view of image capture device 140 that is obscured (e.g., a higher obscured percentage of the field of view may indicate a lower cleanliness rating, decrease by the obscured percentage the cleanliness rating, etc.).

In some non-limiting embodiments or aspects, and referring to FIG. 1C, injection system 104 includes a force sensor 160, (e.g., a motor current sensor, a strain gauge, etc.) in injector 120 that is configured to measure a force associated with moving plunger 156 to deliver fluid from syringe 154. For example, a build-up of contrast and/or dirt within components of injector 120 may increase a force needed to move plunger 156 to deliver fluid from syringe 154. As an example, injection system 104 can determine a numerical cleanliness rating based on a force measured by force sensor 160 that is needed to move plunger 156 to deliver fluid from syringe 154 for one or more injections (e.g., a greater measured force may indicate a lower cleanliness rating, decrement a cleanliness rating, etc.). In such an example, injection system 104 can compare a force measurement of a current or more recent injection to force measurements of previous injections or a calibration measurement to determine the change in the numerical cleanliness rating as a percentage difference in the force measurements.

In some non-limiting embodiments or aspects, and referring to FIG. 1B, injection system 104 includes a force sensor 160, (e.g., a motor current sensor, a strain gauge, etc.) in injector 120 that is configured to measure a force associated with pumping fluids from fluid source 1, 2, . . . N with injector 120. For example, a build-up of contrast and/or dirt within components of injector 120 increases a force needed to pump fluids from fluid source 1, 2, . . . N with injector 120. As an example, injection system 104 can determine a numerical cleanliness rating based on a force measured by force sensor 160 that is needed to deliver fluid from fluid source 1, 2, . . . N with injector 120 to medical device 128 for one or more injections (e.g., a greater measured force may indicate a lower cleanliness rating, decrement a cleanliness rating, etc.). In such an example, injection system 104 can compare a force measurement of a current or more recent injection to force measurements of previous injections or a calibration measurement to determine the change in the numerical cleanliness rating as a percentage difference in the force measurements.

In some non-limiting embodiments or aspects, remote system 106 may include one or more devices capable of receiving data and/or information (e.g., operation data, maintenance data, etc.) from maintenance prediction system 102 and/or injection system 104 via network 108 and/or communicating data and/or information (e.g., operation data, maintenance data, etc) to maintenance prediction system 102 and/or injection system 104 via network 108. For example, remote system 106 may include a computing device, such as a server, a group of servers, and/or other like devices. In some non-limiting embodiments or aspects, remote system 106 may be implemented by or on behalf of an original equipment manufacturer (OEM) of injection system 104 (e.g., an OEM of one or more components or devices of injection system 104, etc.), a provider of injection system 104, an imaging site or a hospital including injection system 104, a service technician assigned to injection system 104, and/or the like.

Network 108 may include one or more wired and/or wireless networks. For example, network 108 may include a cellular network (e.g., a long-term evolution (LTE) network, a third generation (3G) network, a fourth generation (4G) network, a code division multiple access (CDMA) network, etc.), a public land mobile network (PLMN), a local area network (LAN), a wide area network (WAN), a metropolitan area network (MAN), a telephone network (e.g., the public switched telephone network (PSTN)), a private network, an ad hoc network, an intranet, the Internet, a fiber optic-based network, a cloud computing network, a short range wireless communication network (e.g., a Bluetooth network, a near field communication (NFC) network, etc.) and/or the like, and/or a combination of these or other types of networks.

The number and arrangement of systems, devices, and networks shown in FIGS. 1A-1C are provided as an example. There may be additional systems, devices, and/or networks, fewer systems, devices, and/or networks, different systems, devices, and/or networks, or differently arranged systems, devices, and/or networks than those shown in FIGS. 1A-1C. Furthermore, two or more systems or devices shown in FIGS. 1A-1C may be implemented within a single system or a single device, or a single system or a single device shown in FIGS. 1A-1C may be implemented as multiple, distributed systems or devices. Additionally, or alternatively, a set of systems or a set of devices (e.g., one or more systems, one or more devices, etc.) of environment 100 may perform one or more functions described as being performed by another set of systems or another set of devices of environment 100.

Figure 2:
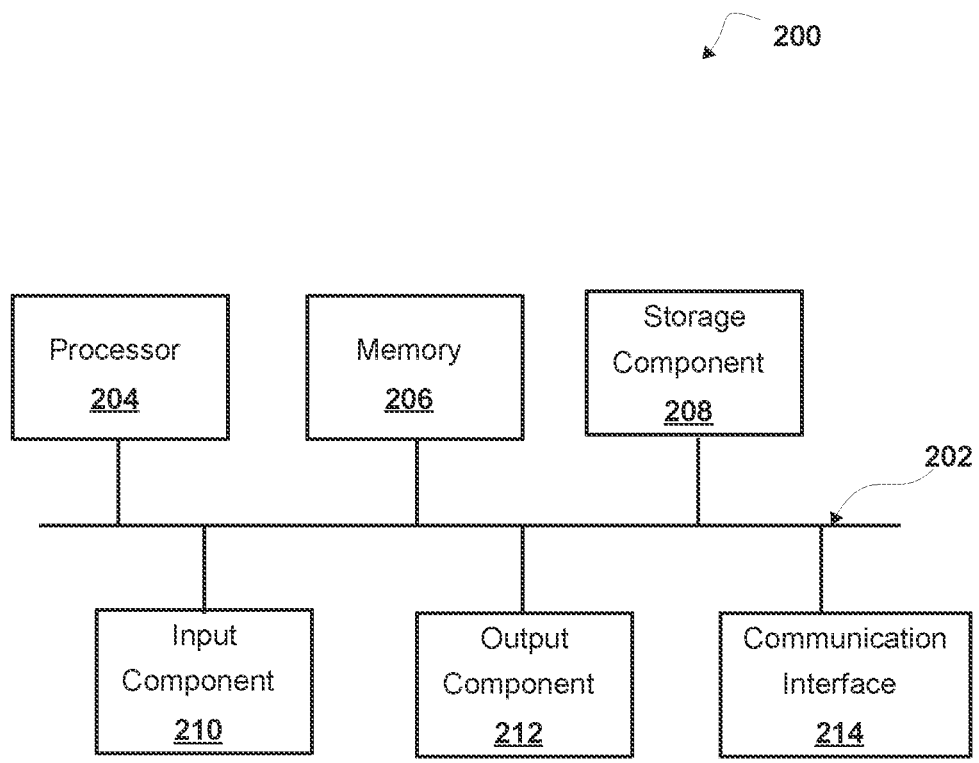
FIG. 2 is a diagram of a non-limiting embodiment or aspect of components of one or more systems or one or more devices of FIGS. 1A-1C.

Referring now to FIG. 2, FIG. 2 is a diagram of example components of a device 200. Device 200 may correspond to one or more devices and/or one or more systems of maintenance prediction system 102, one or more devices and/or one or more systems of injection system 104, and/or one or more devices and/or one or more systems of remote system 106. In some non-limiting embodiments or aspects, maintenance prediction system 102, injection system 104, and/or remote system 106 can include at least one device 200 and/or at least one component of device 200. As shown in FIG. 2, device 200 may include a bus 202, a processor 204, memory 206, a storage component 208, an input component 210, an output component 212, and a communication interface 214.

Bus 202 may include a component that permits communication among the components of device 200. In some non-limiting embodiments or aspects, processor 204 may be implemented in hardware, firmware, or a combination of hardware and software. For example, processor 204 may include a processor (e.g., a central processing unit (CPU), a graphics processing unit (GPU), an accelerated processing unit (APU), etc.), a microprocessor, a digital signal processor (DSP), and/or any processing component (e.g., a field-programmable gate array (FPGA), an application-specific integrated circuit (ASIC), etc.) that can be programmed to perform a function. Memory 206 may include random access memory (RAM), read only memory (ROM), and/or another type of dynamic or static storage device (e.g., flash memory, magnetic memory, optical memory, etc.) that stores information and/or instructions for use by processor 204.

Storage component 208 may store information and/or software related to the operation and use of device 200. For example, storage component 208 may include a hard disk (e.g., a magnetic disk, an optical disk, a magneto-optic disk, a solid state disk, etc.), a compact disc (CD), a digital versatile disc (DVD), a floppy disk, a cartridge, a magnetic tape, and/or another type of computer-readable medium, along with a corresponding drive.

Input component 210 may include a component that permits device 200 to receive information, such as via user input (e.g., a touch screen display, a keyboard, a keypad, a mouse, a button, a switch, a microphone, etc.). Additionally, or alternatively, input component 210 may include a sensor for sensing information (e.g., a global positioning system (GPS) component, an accelerometer, a gyroscope, an actuator, etc.). Output component 212 may include a component that provides output information from device 200 (e.g., a display, a speaker, one or more light-emitting diodes (LEDs), etc.).

Communication interface 214 may include a transceiver-like component (e.g., a transceiver, a separate receiver and transmitter, etc.) that enables device 200 to communicate with other devices, such as via a wired connection, a wireless connection, or a combination of wired and wireless connections. Communication interface 214 may permit device 200 to receive information from another device and/or provide information to another device. For example, communication interface 214 may include an Ethernet interface, an optical interface, a coaxial interface, an infrared interface, a radio frequency (RF) interface, a universal serial bus (USB) interface, a Wi-Fi® interface, a cellular network interface, and/or the like.

Device 200 may perform one or more processes described herein. Device 200 may perform these processes based on processor 204 executing software instructions stored by a computer-readable medium, such as memory 206 and/or storage component 208. A computer-readable medium (e.g., a non-transitory computer-readable medium) is defined herein as a non-transitory memory device. A memory device includes memory space located inside of a single physical storage device or memory space spread across multiple physical storage devices.

Software instructions may be read into memory 206 and/or storage component 208 from another computer-readable medium or from another device via communication interface 214. When executed, software instructions stored in memory 206 and/or storage component 208 may cause processor 204 to perform one or more processes described herein. Additionally, or alternatively, hardwired circuitry may be used in place of or in combination with software instructions to perform one or more processes described herein. Thus, embodiments or aspects described herein are not limited to any specific combination of hardware circuitry and software.

The number and arrangement of components shown in FIG. 2 are provided as an example. In some non-limiting embodiments or aspects, device 200 may include additional components, fewer components, different components, or differently arranged components than those shown in FIG. 2.

Additionally, or alternatively, a set of components (e.g., one or more components) of device 200 may perform one or more functions described as being performed by another set of components of device 200.

Figure 3:
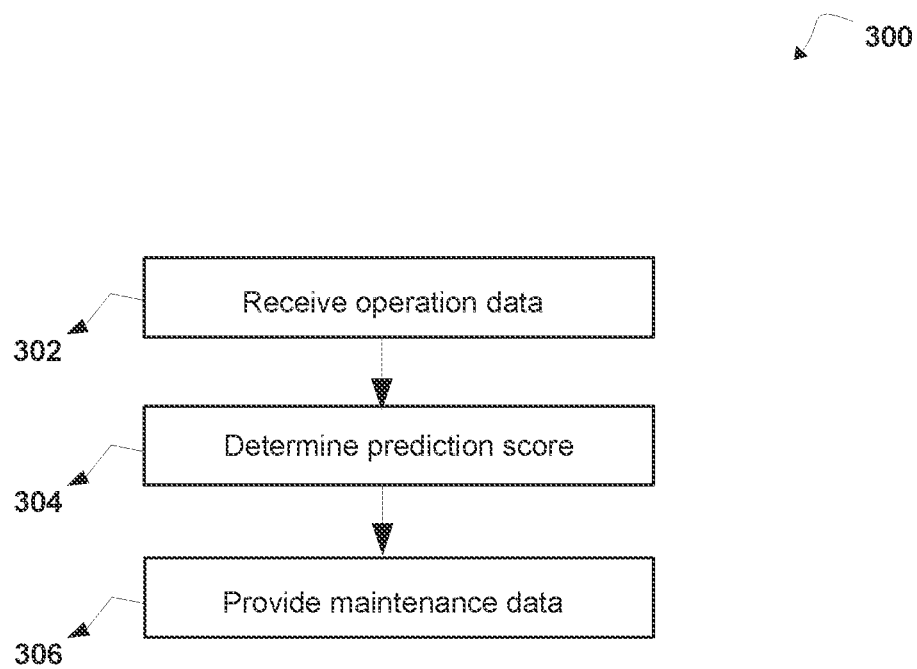
FIG. 3 is a flowchart of a non-limiting embodiment or aspect of a process for predictive maintenance.

Referring now to FIG. 3, FIG. 3 is a flowchart of a non-limiting embodiment or aspect of a process 300 for predictive maintenance of injection systems. In some non-limiting embodiments or aspects, one or more of the steps of process 300 are performed (e.g., completely, partially, etc.) by maintenance prediction system 102 (e.g., one or more devices of maintenance prediction system 102, etc.) In some non-limiting embodiments or aspects, one or more of the steps of process 300 are performed (e.g., completely, partially, etc.) by another device or a group of devices separate from or including maintenance prediction system 102, such as injection system 104 (e.g., one or more devices of injection system 104, eta) and/or remote system 106 (e.g., one or more devices of remote system 106, etc.).

As shown in FIG. 3, at step 302, process 300 includes receiving operation data associated with one or more injection systems. For example, maintenance prediction system 102 receives operation data associated with injection system 104. As an example, maintenance prediction system 102 can receive operation data associated with injection system 104 from injection system 104, remote system 106, and/or one or more other devices associated with an operation, a medical procedure, a patient, and/or a user or operator associated with injection system 104 (e.g., a power supply system, an imaging device or scanner, such as a computed tomography (CT) system, a magnetic resonance imaging (MRI) system, and/or the like, a patient device, such as a patient identification device (e.g., a wearable RFID tag and/or a computing device, etc.) including a patient identifier and/or patient information, a heart rate monitor, and/or the like, a user or operator device, such as a user or operator identification device (e.g., a wearable RFID tag and/or a computing device, etc.) including a user or operator identifier and/or user or operator information, and/or the like, etc.). In such an example, injection system 104, remote system 106, and/or the one or more other medical devices may include one or more sensors, one or more input components, one or more output components, and/or the like that are capable of receiving, determining, measuring, sensing, and/or providing operation data associated with a function, a medical procedure, a patient, and/or a user or operator associated with injection system 104 (e.g., a function, a medical procedure, a patient, and/or a user or operator associated with one or more operations of injection system 104, etc.). In some non-limiting embodiments or aspects, maintenance prediction system 102 receives operation data associated with injection system 104 in a continuous manner, in a periodic manner, in response to a user request for a predictive maintenance analysis, a diagnostic operation, and/or a benchmarking service to be performed in association with injection system 104, automatically in response to a boot-up operation and/or another operation performed by injection system 104, and/or the like.

In some non-limiting embodiments or aspects, operation data includes one or more operation parameters associated with one or more operations of one or more injection systems. For example, operation data can include one or more operation parameters associated with one or more operations of injection system 104. As an example, an operation of an injection system can include at least one of the following operations or functions: a software operation or function (e.g., receiving, installing, modifying, updating, initiating, executing, and/or monitoring one or more software applications, etc.) a hardware operation or function (e.g., receiving, installing, modifying, updating, powering, operating, and/or monitoring one or more hardware components or devices, such as a microprocessor, a memory, a storage component, an input component, an output component, a circuit board, a sensor, a pump, a valve, and/or the like, etc.), a mechanical operation or function (e.g., receiving, providing, modifying, and/or monitoring a fluid flow and/or delivery of a fluid to a medical device and/or a patient, etc.), an electrical operation or function (e.g., receiving, providing, consuming, and/or monitoring a supply of power, etc.), a user interface operation or function (e.g., providing a user interface via output component 212, receiving user input via input component 210, etc.), a communications operation or function (e.g., receiving, modifying, updating, storing, providing, and/or monitoring operation data and/or maintenance data, etc.), or any combination thereof. In such an example, an operation parameter may include a parameter received, determined, measured, sensed, and/or provided in association with a function, a medical procedure, a patient, and/or a user or operator associated with injection system 104 (e.g., a function, a medical procedure, a patient, and/or a user or operator associated with one or more operations of injection system 104, etc.).

In some non-limiting embodiments or aspects, an operation parameter can include at least one of the following parameters associated with an injection system (e.g., at least one of the following parameters associated with one or more components or devices of an injection system, etc.): a flow rate during one or more injections (e.g., a maximum, a minimum, an average, a total, etc.), a flow rate programmed to be achieved for one or more injections, a volume pumped and/or delivered during one or more injections (e.g., a maximum, a minimum, an average, a total, etc.), a volume programmed to be delivered during one or more injections, a duration of time of one or more injections (e.g., a maximum, a minimum, an average, a total, etc.), a difference between the flow rate during the one or more injections and a programmed flow rate (e.g., set by an injection parameter of an injection protocol, etc.) of the one or more injections, a difference between the volume pumped and/or delivered during the one or more injections and a programmed volume to be pumped and/or to be delivered (e.g., set by an injection parameter of an injection protocol, etc.) during the one or more injections, a number of injections performed, an achieved pressure of one or more injections (e.g., a maximum, a minimum, an average, a total, etc.), a difference between the achieved pressure of the one or more injections and a programmed pressure to be achieved (e.g., set by an injection parameter of an injection protocol, etc.) during the one or more injections, a pressure limit or threshold beyond which the injection system is programmed to cease delivery an injection, a duration of time powered-on (e.g., a maximum, a minimum, an average, a total, etc.), a number of times power has been cycled, an energy consumption (e.g., a maximum, a minimum, an average, a total, etc.), a linear amount of power delivered or used (e.g., an integral of ((pressure)*(flow rate))/(time), etc.), a non-linear amount of power delivered or used (e.g., an integral of a f(pressure)* (time), etc.), a voltage (e.g., a maximum, a minimum, an average, a total, etc.), a resistance, a current, a noise or signal level, a mechanical force produced and/or the like (e.g., a maximum, a minimum, an average, a total, etc.) by a motor of the injection system, a number of camera reads, an existence or operability of communications with one or more other systems or devices, a number and/or type of error codes received, a number, a duration and/or a type of user interface keys actuated (e.g., pressed, etc.), power line conditions, a temperature and/or a humidity within an injection system (e.g., a maximum, a minimum, an average, a total, etc.), a temperature and/or a humidity of an environment surrounding an injection system (e.g., a maximum, a minimum, an average, a total, etc.), a vibration frequency and/or amplitude (e.g., a maximum, a minimum, an average, a total, etc.), a movement above a threshold movement (e.g., as measured by an accelerometer, etc.), a number of times cleaned, a staff rating of wear (e.g., a numerical rating, etc.), a staff rating of cleanliness (e.g., a numerical rating, etc.), a service record of service (e.g., a number of services performed, a type of services performed, etc.), a system rating of wear (e.g., a numerical rating, etc.), a system rating of cleanliness (e.g., a numerical rating, etc.), a number of one or more disposables (e.g., syringes, transfer sets, etc.) sold to and/or used by an associated customer, an amount of contrast used, a type of contrast used, a vial size of contrast used, a number of injection systems at an imaging site including the injection system, a turnover rate of users or operators associated with an imaging site including the injection system, an identifier of a user or operator associated with one or more operations or uses of the injection system, an identifier of a customer associated with an imaging site including the injection system, an indication of liquid within the injection system (e.g., as detected or measured by one or more liquid sensors, etc.), an amount (e.g., a maximum, a minimum, an average, a total, etc.) of x-ray radiation, RF exposure, magnetic field exposure, and/or the like in an environment surrounding the injection system, one or more injection protocols used for one or more injections, and/or the like.

In some non-limiting embodiments or aspects, operation data associated with injection system 104 includes one or more exemplary data types, information types, and/or parameters that are disclosed in U.S. patent application Ser. No. 10/143,562, filed on May 10, 2002, issued as U.S. Pat. No. 7,457,804; U.S. patent application Ser. No. 12/254,318, filed on Oct. 20, 2008, issued as U.S. Pat. No. 7,996,381; U.S. patent application Ser. No. 13/180,175, filed on Jul. 11, 2011, issued as U.S. Pat. No. 8,521,716; International Patent Application Publication No. WO2017/027724A1, published Feb. 16, 2017, which was filed as International Application No. PCT/US2016/046587 on Aug. 11, 2016; and International Patent Application Publication No. WO2017/040152A1, published Mar. 9, 2017, which was filed as International Application No. PCT/US2016/048441 on Aug. 24, 2016, the disclosures of each of which are incorporated herein by reference in their entireties.

As further shown in FIG. 3, at step 304, process 300 includes determining one or more prediction scores for the one or more injection systems based on the operation data. For example, maintenance prediction system 102 determines one or more prediction scores for injection system 104 based on the operation data. As an example, maintenance prediction system 102 determines one or more prediction scores for injection system 104 based on the operation data in a continuous manner, in a periodic manner, in response to a user request for a predictive maintenance analysis, a diagnostic operation, and/or a benchmarking service to be performed in association with injection system 104, automatically in response to a boot-up operation and/or another operation performed by injection system 104, and/or the like.

In some non-limiting embodiments or aspects, the one or more prediction scores include one or more predictions of one or more operation failures or misuses for injection system 104. For example, a prediction score includes an indication (e.g., a score, a number, a ranking, a probability, a likelihood, etc.) of an operation failure or misuse occurring for injection system 104. As an example, an operation failure or misuse may include a failure or a misuse of injection system 104 (e.g., a failure or a misuse of one or more operations of injection system 104, a failure or misuse of one or more devices and/or one or more components of one or more devices of injection system 104, etc.). In such an example, an operation failure of injection system 104 may include at least one of the following: a software failure, a hardware failure, a component or device failure, and/or the like that causes injection system 104 to operate contrary to one or more predefined operation thresholds. For example, an operation failure may require service, repair, and/or replacement of the software, the hardware, the component or device, and/or the like affected by the operation failure in order for injection system 104 to operate in a proper manner. In such an example, an operation misuse of injection system 104 may include at least one of the following: an input to, a configuration of, an operation of, and/or the like by a user or operator of injection system 104 that causes injection system 104 to operate contrary to one or more predefined operation thresholds.

In some non-limiting embodiments or aspects, maintenance prediction system 102 determines the one or more prediction scores based on one or more machine learning techniques (e.g., a pattern recognition technique, a data mining technique, a heuristic technique, a supervised learning technique, an unsupervised learning technique, etc.). For example, maintenance prediction system 102 generates one or more models (e.g., an estimator, a classifier, a prediction model, an operation failure or misuse prediction model, a maintenance prediction model, etc.) based on one or more machine learning algorithms (e.g., a decision tree algorithm, a gradient boosted decision tree algorithm, a neural network algorithm, a convolutional neural network algorithm, a random forest algorithm, etc.), In such an example, maintenance prediction system 102 generates the one or more prediction scores using the one or more models.

In some non-limiting embodiments or aspects, the one or more predictive models are designed to receive, as an input, operation data associated with injection system 104 and, provide, as an output a prediction (e.g., a probability, a binary output, a percentage, a yes-no output, a score, a prediction score, etc.) as to one or more operation failures or misuses of injection system 104. For example, maintenance prediction system 102 generates one or more predictive models for predicting one or more operation failures or misuses of one or more injection systems. As an example, maintenance prediction system 102 can generate the one or more predictive models to determine one or more prediction scores that include a prediction of whether one or more operation failures or misuses of one or more injection systems (e.g., of one or more components or devices of one or more injection systems, etc.) will occur within a time period and/or a number of uses of the one or more injection systems.

In some non-limiting embodiments or aspects, maintenance prediction system 102 stores the one or more predictive models (e.g., stores the model(s) for later use, etc.). In some non-limiting embodiments or aspects, maintenance prediction system 102 stores the one or more predictive models in a data structure (e.g., a database, a linked list, a tree, etc.). In some non-limiting embodiments or aspects, the data structure is located within maintenance prediction system 102 or external to (e.g., remote from, etc.) maintenance prediction system 102.

In some non-limiting embodiments or aspects, maintenance prediction system 102 processes operation data (e.g., operation data associated with injection system 104, operation data associated with a plurality of injection system 104, etc.) to obtain training data for the one or more models. For example, maintenance prediction system 102 processes operation data to change the operation data into a format that is analyzed (e.g., by maintenance prediction system 102) to generate the one or more models. The operation data that is changed is referred to as training data. In some implementations, maintenance prediction system 102 processes the operation data to obtain the training data based on receiving the operation data. Additionally, or alternatively, maintenance prediction system 102 processes the operation data to obtain the training data based on the system 102 receiving an indication from a user thereof that the system 102 is to process the operation data, such as when maintenance prediction system 102 receives an indication to create a model.

In some non-limiting embodiments or aspects, maintenance prediction system 102 processes the operation data by determining one or more variables based on the operation data. In some non-limiting embodiments or aspects, a variable includes a metric, associated with an operation failure or misuse of injection system 104, which may be derived based on the operation data. The variable is analyzed to generate a model. For example, the variable includes a variable associated with one or more operation parameters of injection system 104.

In some non-limiting embodiments or aspects, maintenance prediction system 102 analyzes the training data to generate a model (e.g., the one or more prediction models). For example, maintenance prediction system 102 uses machine learning techniques to analyze the training data to generate the model. In some implementations, generating the model (e.g., based on training data obtained from operation data, based on training data obtained from pre-existing operation data, etc.) is referred to as training the model. The machine learning techniques include, for example, supervised and/or unsupervised techniques, such as decision trees (e.g., gradient boosted decision trees, etc.), logistic regressions, artificial neural networks (e.g., convolutional neural networks, etc.), Bayesian statistics, learning automata, Hidden Markov Modeling, linear classifiers, quadratic classifiers, association rule learning, random forests, and/or the like. In some non-limiting embodiments or aspects, the model includes a prediction model that is specific to a particular injection system 104, a particular plurality of injection systems 104, a particular operation parameter, a particular plurality of operation parameters, a particular operation failure and/or misuse, a particular plurality of operation failures and/or misuses and/or the like. Additionally, or alternatively, the prediction model is specific to a particular user or operator (e.g., a particular user or operator of injection system 104, a particular imaging site including injection system 104, a particular customer that operates injection system 104, etc.).

Additionally, or alternatively, when analyzing the training data, maintenance prediction system 102 identifies one or more variables (e.g., one or more independent variables) as predictor variables that are used to make a prediction (e.g., when analyzing the training data). In some implementations, values of the predictor variables are inputs to the model. For example, maintenance prediction system 102 identifies a subset (e.g., a proper subset) of variables as predictor variables that are used to accurately predict one or more operation failures or misuses for an injection system. In some implementations, the predictor variables include one or more of the variables (e.g., one or more of the operation parameters, etc.) as discussed above that have a significant impact (e.g., an impact satisfying a threshold) on a probability that the operation failure or misuse occurs for the injection system within the time period or the number of uses of the injection system.

In some non-limiting embodiments or aspects, maintenance prediction system 102 validates the model. For example, maintenance prediction system 102 validates the model after maintenance prediction system 102 generates the model. In some implementations, maintenance prediction system 102 validates the model based on a portion of the training data to be used for validation. For example, maintenance prediction system 102 partitions the training data into a first portion and a second portion, where the first portion is used to generate the model, as described above. In this example, the second portion of the training data (e.g., the validation data) is used to validate the model. In some non-limiting embodiments or aspects, the first portion of the training data is different from the second portion of the training data.

In some non-limiting embodiments or aspects, maintenance prediction system 102 validates the model by providing validation data including operation data that includes a plurality of operation parameters of a plurality of injection systems as input to the model, and determining, based on an output of the prediction model, whether the prediction model correctly, or incorrectly, predicted the one or more operation failures or misuses of the plurality of injection systems. In some implementations, maintenance prediction system 102 validates the model based on a validation threshold (e.g., a threshold value of the validation data). For example, maintenance prediction system 102 is configured to validate the model when an operation failure or misuse of an injection system (e.g., an operation failure or misuse within a time period or a number of uses of the injection system, etc.) is correctly predicted by the model (e.g., when the prediction model correctly predicts 50% of the validation data, when the prediction model correctly predicts 70% of the validation data, etc.). In some non-limiting embodiments or aspects, if maintenance prediction system 102 does not validate a model (e.g., when a percentage of validation data does not satisfy the validation threshold), maintenance prediction system 102 generates additional prediction models.

In some non-limiting embodiments or aspects, if the one or more models have been validated, maintenance prediction system 102 further trains the one or more models and/or creates new models based on receiving new training data. In some non-limiting embodiments or aspects, the new training data includes operation data associated with a plurality of injection system 104 that is different from a previous plurality of injection system 104 previously used to train the one or more models.

In some non-limiting embodiments or aspects, predictions from multiple machine learning algorithms may be combined to build an ensemble of algorithms or predictive models to increase predictive power. In such an example, maintenance prediction system 102 selects a machine learning algorithm or model from a plurality of machine learning algorithms or models based on an ability of the algorithm or model to predict the training data. For example, maintenance prediction system 102 may compare an accuracy of the various models in predicting the training data. In such an example, maintenance prediction system 102 may build an ensemble model by averaging predictions of selected models, comparing plots with sum of squares of the residuals to individual models, and selecting an ensemble model or an individual model based on the comparison.

In some non-limiting embodiments or aspects, maintenance prediction system 102 determines the one or more prediction scores based on one or more measurements of a flow rate and a volume delivered by injection system 104. As an example, maintenance prediction system 102 can receive operation data including a measurement (e.g., a measurement that is independent of a type of pump, including non-positive displacement pumps, etc.) of a flow rate of one or more injections with injection system 104 and a total volume delivered via the one or more injections with injection system 104 (e.g., measurements from flow rate sensor 124 of injection system 104 used in a feedback control loop between flow rate sensor 124 and pump 120, etc.) and apply one or more models and/or one or more equations or formulas (e.g., a cube root life equation, etc.) to the operation data to determine a prediction score for a prediction of a remaining time of use and/or a remaining number of uses of injection system 104 until an operation failure or misuse. In such an example, maintenance prediction system 102 can apply a cube root life equation in which a maximum achieved pressure can be substituted for average load, and the injection volume and the flow rate can be used to establish duration of load to determine the prediction score.

In some non-limiting embodiments or aspects, maintenance prediction system 102 determines the one or more prediction scores using a pattern prediction model. For example, maintenance prediction system 102 can receive operation data including operation parameters associated with objective factors of injection system wear (e.g., one or more temperatures over one or more time periods within injection system 104 and/or in an environment surrounding injection system 104, one or more vibrations over one or more time periods within injection system 104, etc.) and/or operation parameters associated with subjective factors of injection system wear (e.g., a rating associated with staff handling of injection system 104, etc), input the operation data to a pattern prediction model, and receive, as output, a prediction score for a prediction of a remaining time of use and/or a remaining number of uses of injection system 104 until an operation failure or misuse. As an example, maintenance prediction system 102 can alert hospital administration when a nonrandom pattern is recognized in a service history of injection system 104. In such an example, pattern recognition system can be cross-linked to hospital staffing records to identify the user or operator (e.g., the hospital personnel, etc.) on duty when a problem is reported. In some non-limiting embodiments or aspects, maintenance prediction system 102 can automatically recalibrate and/or regulate a duty cycle or other operation of injection system 104 based on the prediction score in an attempt to mitigate the predicted operation failure or misuse.

In some non-limiting embodiments or aspects, maintenance prediction system 102 determines one or more prediction scores for injection system 104 based on one or more comparisons of operation data associated with injection system 104 to operation data associated with a plurality of other injection systems. For example, maintenance prediction system can aggregate operation data from a plurality of injection systems 104 (e.g., from injection systems at a same location, from injection systems at a same imaging site, from injection systems at different remote locations, from injection systems at different imaging sites, etc.), and compare operation data of one or more injection systems of the plurality of injection systems 104 to operation data of one or more other injection systems of the plurality of injection systems 104. As an example, maintenance prediction system 102 can provide as a prediction score a comparison (e.g., a numerical difference, etc.) between operation data (e.g., service records, a number of times injection system 104 has been serviced, etc.) of one or more injection systems (e.g., injection systems at an imaging site operated by a customer, etc.) and operation data of one or more other injection systems (e.g., a global database of injection systems at imaging sites operated by one or more other customers, etc.). In such an example, maintenance prediction system 102 can determine if the one or more injection systems of the customer are experiencing a substantially different number of operation failures or misuses (e.g., that satisfies a threshold difference, etc,) as compared to a number of operation failures or misuses experienced by the one or more other injection systems (e.g., as to other customers and/or other imaging sites of the same customer, etc.). For example, maintenance prediction system 102 can use service benchmarking to indicate how injection system 104 associated with a customer or hospital compares to injection systems associated with other customers or hospitals (e.g., how operation and/or use of injection system 104 compares to other injection systems, etc.), In such an example, maintenance prediction system 102 can determine a cost savings associated with implementing one or more maintenance actions performed for and/or with injection system 104. For example, maintenance prediction system 102 can determine the cost savings as a cost of an amount of contrast saved by decreasing contrast waste by implementing the one or more maintenance actions as compared to one or more other injection systems.

In some non-limiting embodiments or aspects, maintenance prediction system 102 determines the one or more prediction scores based on an energy consumption of one or more injection systems. For example, maintenance prediction system 102 can apply, as input, an energy consumption of injection system 104 to one or more prediction models and/or one or more look-up tables, formulas, and/or thresholds, and receive, as output, a prediction score for a prediction of a remaining time of use and/or a remaining number of uses of injection system 104 until an operation failure or misuse. For example, maintenance prediction system 102 can automatically recalibrate and/or regulate a duty cycle or other operation of injection system 104 based on the prediction score in an attempt to mitigate the predicted operation failure or misuse. As an example, maintenance prediction system 102 can automatically schedule a service technician (e.g., dispatch a service technician to injection system 104, etc.) in response to an energy consumption of injection system 104 satisfying a threshold that indicates injection system 104 is reaching an end of its expected service life and/or that imminent failure of injection system 104 is expected.

In some non-limiting embodiments or aspects, maintenance prediction system 102 determines the one or more prediction scores based on a customer specific usage of one or more injection systems. For example, maintenance prediction system 102 can receive usage-based operation parameters (e.g., a number of one or more disposables (e.g., syringes, transfer sets, etc.) used in association with injection system 104, an amount, a type, a vial size, and/or the like of contrast agent used in association with injection system 104), regional regulations and/or practices associated with injection system 104 that indicate a threshold for the one or more usage-based operation parameters, an indication of a lack of contrast warning, a number of injection systems associated with a customer, a turnover rate of users or operators of injection system 104, a competence rating of users or operators associated with injection system 104, and/or the like. As an example, maintenance prediction system 102 can apply, as input, the one or more usage-based operation parameters to one or prediction models and/or one or more look-up tables, formulas, and/or thresholds, and receive, as output, a prediction score for a prediction of a remaining time of use and/or a remaining number of uses of injection system 104 until an operation failure or misuse. In some non-limiting embodiments or aspects, maintenance prediction system 102 can determine a tailored preventative service plan for the customer based on the predicted reliability of injection system 104.

In some non-limiting embodiments or aspects, maintenance prediction system determines the one or more prediction scores based on a contrast fouling score system. For example, maintenance prediction system 102 can receive one or more ratings associated with a cleanliness of injection system 104.

In some non-limiting embodiments or aspects, injection system 104 can provide (e.g., via a user interface with output component 212, etc.) a prompt that requests a user or operator of injection system 104 to input (e.g., via a user interface associated with input component 210) a rating (e.g., on a numerical scale, etc.) of a cleanliness of injection system 104. In such an example, injection system 104 can provide the prompt before, during, and/or after each operation and/or injection procedure with injection system 104, at periodic intervals, in response to a user request to rate the cleanliness, and/or the like. In some non-limiting embodiments or aspects, maintenance prediction system 102 applies, as input, the one or more cleanliness ratings, to one or prediction models and/or one or more look-up tables, formulas, and/or thresholds, and receives, as output, a prediction score for a prediction of a remaining time of use and/or a remaining number of uses of injection system 104 until an operation failure or misuse. For example, maintenance prediction system 102 can automatically recalibrate and/or regulate a duty cycle or other operation of injection system 104 based on the prediction score in an attempt to mitigate the predicted operation failure or misuse. As an example, maintenance prediction system 102 can automatically schedule a service technician (e.g., dispatch a service technician to injection system 104, etc.) in response to an aggregate cleanliness rating of injection system 104 satisfying a threshold. In some non-limiting embodiments or aspects, maintenance prediction system 102 can associate prediction scores of a plurality of injection systems 104 determined based on cleanliness ratings with identifiers of users or operators that operate the injection systems to compare the users or operators to each other with respect to the cleanliness ratings of their systems.

In some non-limiting embodiments or aspects, injection system 104 can determine a rating (e.g., on a numerical scale, etc.) of a cleanliness of injection system 104. For example, injection system 104 can determine the rating of the cleanliness of injection system 104 based on one or more scans of at least one bar code (BC) by optical sensor 158 and/or image capture device 140, one or more images of a field of view of image capture device 140, one or more force measurements measured by force sensor 160, or any combination thereof. In such an example, injection system 104 can capture the scans, images, and/or force measurements before, during, and/or after each operation and/or injection procedure with injection system 104, at periodic intervals, in response to a user request to rate the cleanliness, and/or the like. In some non-limiting embodiments or aspects, maintenance prediction system 102 applies, as input, the one or more cleanliness ratings, to one or prediction models and/or one or more look-up tables, formulas, and/or thresholds, and receives, as output, a prediction score for a prediction of a remaining time of use and/or a remaining number of uses of injection system 104 until an operation failure or misuse. For example, maintenance prediction system 102 can automatically recalibrate and/or regulate a duty cycle or other operation of injection system 104 based on the prediction score in an attempt to mitigate the predicted operation failure or misuse. As an example, maintenance prediction system 102 can automatically schedule a service technician (e.g., dispatch a service technician to injection system 104, etc.) in response to an aggregate cleanliness rating of injection system 104 satisfying a threshold. In some non-limiting embodiments or aspects, maintenance prediction system 102 can associate prediction scores of a plurality of injection systems 104 determined based on cleanliness ratings with identifiers of users or operators that operate the injection systems to compare the users or operators to each other with respect to the cleanliness ratings of their systems.

As further shown in FIG. 3, at step 306, process 300 includes providing maintenance data associated with the one or more operation failures or misuses. For example, maintenance prediction system 102 provides maintenance data associated with the one or more operation failures or misuses. As an example, maintenance prediction system 102 provides maintenance data associated with the one or more operation failures or misuses to a user or operator of injection system 104 (e.g., via a user interface provided by output component 212 of maintenance prediction system 102, via a user interface provided by output component 212 of injection system 104, etc.), to injection system 104, to remote system 106 (e.g., to a computing system implemented by or on behalf of an original equipment manufacturer (OEM) of injection system 104 (e.g., an OEM of one or more components or devices of injection system 104, etc.), to a computing system implemented by or on behalf of a provider of injection system 104 (e.g., the MEDRAD® Stellant CT Injection System with Certegra® Workstation is provided by Bayer, etc.), to a computing system implemented by on or behalf of an imaging site, a customer, or a hospital, etc.), and/or the like.

In some non-limiting embodiments or aspects, maintenance prediction system 102 provides maintenance data to a user or operator, an injection system, and/or a remote computing system or entity based on an identifier of the user or operator, an identifier of the injection system, and/or an identifier of the remote computing system or entity being included in the maintenance data and/or operation data used to determine one or more prediction scores upon which the maintenance data is based. In some non-limiting embodiments or aspects, a type and/or amount of the maintenance data provided is based on a recipient of the maintenance data.

In some non-limiting embodiments or aspects, maintenance data includes operation data (e.g., one or more operation parameters associated with one or more operations of injection system 104, etc.) and/or data associated with one or more maintenance actions (e.g., a prompt to a user or operator to perform one or more maintenance actions, an instruction that causes injection system 104 to perform one or more maintenance actions, an indication that one or more maintenance actions have been scheduled to be performed for and/or with injection system 104, an indication that one or more maintenance actions have been performed for and/or with injection system 104, a list of other injection systems of a plurality of injection systems at an imaging site including injection system 104, one or more maintenance agreements associated with injection system 104, etc.).

In some non-limiting embodiments or aspects, maintenance data is based on the one or more prediction scores. For example, maintenance prediction system 102 can determine maintenance data based on the one or more prediction scores. As an example, maintenance prediction system 102 can query a look-up table or database that associates one more maintenance actions with one or more predicted operation failures or misuses of injection system 104 (e.g., one or more predicted operation failures or misuses of one or more components or devices of injection system 104, etc.) based on the one or more prediction scores. In such an example, maintenance prediction system 102 can retrieve and/or provide maintenance data associated with one or more maintenance actions for the one or more operations failures or misuses of injection system 104 having one or more prediction scores that satisfy one or more threshold scores.

In some non-limiting embodiments or aspects, maintenance data includes an instruction that causes injection system 104 to automatically perform one or more maintenance actions. For example, a maintenance action includes at least one of the following actions performed automatically with injection system 104 (e.g., with one or more components or devices of injection system 104, etc.): providing a prompt to a user (e.g., via a user interface of output component 212, etc.) to perform one or more maintenance actions for injection system 104, scheduling a service technician (e.g., dispatching a service technician to injection system 104, etc.) to repair, service, and/or replace injection system 104, automatically placing an order for one or more disposables (e.g., syringes, transfer sets, etc.) and/or one more contrast agents, providing instructions (e.g., via a user interface of output component 212, etc.) to a user or operator to use injection system 104 in specific manner to avoid a specific operation failure and/or misuse of injection system 104, providing a recommendation (e.g., via a user interface of output component 212, etc.) to improve service based on a comparison of injection system 104 to one or more other injection systems, providing (e.g., via a user interface of output component 212, etc.) a volume used, a volume remaining, a pressure limit, and/or the like associated with injection system 104, offering (e.g., via a user interface of output component 212, etc.) a service plan based on usage-based operation parameters of injection system 104, offering (e.g., via a user interface of output component 212, etc.) a customized preventative maintenance service (e.g., cleaning, calibration of a power supply, motors, etc.), recommending (e.g., via a user interface of output component 212, etc.) training to a user or operator, rebooting software, updating software, transmitting operation data and/or an alert to remote system 106, measuring component degradation, wear, or cleanliness, providing remote entry to a remote computing system to modify and/or update software and/or one or more operation parameters, disabling or limiting one or more operations or functions (e.g., disabling injections with operation parameters that define a flow rate that satisfies a threshold flow rate and/or a pressure that satisfies a threshold pressure, etc.), disabling power, stopping an injection, cycling power, prompting a customer to transmit a request for service directly from injection system 104, and/or the like.

In some non-limiting embodiments or aspects, maintenance prediction system 102 determines the one or more prediction scores for injection system 104 and/or provides maintenance data associated with the one or more prediction scores in a continuous manner, in a periodic manner, automatically in response to a boot-up operation and/or another operation performed by injection system 104, and/or the like.

Although the invention has been described in detail for the purpose of illustration based on what is currently considered to be the most practical and preferred embodiments or aspects, it is to be understood that such detail is solely for that purpose and that the invention is not limited to the disclosed embodiments or aspects, but, on the contrary, is intended to cover modifications and equivalent arrangements that are within the spirit and scope of the appended claims. For example, it is to be understood that the present invention contemplates that, to the extent possible, one or more features of any embodiment or aspect can be combined with one or more features of any other embodiment or aspect,

The invention claimed is:

1. A predictive maintenance system comprising:
one or more injection systems including an injector including a motor configured to one of: (i) move a plunger via a respective piston element to deliver fluid from a syringe of the injector and (ii) power a pump to pump fluids from a fluid source of the injector;
one or more vibration monitoring sensors configured to measure a vibration frequency and/or amplitude of the injector motor of the injector during one of: (i) moving, with the motor, the plunger to deliver fluid from the syringe of the injector and (ii) powering, with the motor, the pump to pump fluids from the fluid source of the injector, for the one or more injection systems for one or more injection operations;
a computer system comprising one or more processors programmed or configured to:
receive operation data associated with the one or more injection systems, wherein the operation data includes one or more operation parameters associated with one or more operations of the one or more injection systems, and wherein the one or more operation parameters include for each of the one or more injection systems the vibration frequency and/or amplitude of the injector motor thereof measured by the one or more vibration monitoring sensors for the one or more injection operations;
determine one or more prediction scores for the one or more injection systems based on the operation data including for each of the one or more injection systems the vibration frequency and/or amplitude of the injector motor thereof measured by the one or more vibration monitoring sensors for the one or more injection operations, wherein the one or more prediction scores include one or more predictions of one or more operation failures or misuses for the one or more injection systems associated with a build-up of wear, contrast, and/or dirt in connection therewith, such that an effect of the build-up of wear, contrast, and/or dirt for each of the one or more injection systems is determined by applying a pattern prediction model to the vibration frequency and/or amplitude of the injector motor thereof measured by the one or more vibration monitoring sensors;
provide maintenance data associated with the one or more operation failures or misuses, wherein the maintenance data is determined based on the one or more prediction scores, wherein the maintenance data includes a prediction of a remaining time of use and/or a remaining number of uses for the one or more injection systems until one or more operation failures or misuses for the one or more injection systems associated with a build-up of wear, contrast, and/or dirt in connection therewith; and automatically disable, based on the maintenance data, the one or more injection systems from performing an injection operation.

2. The predictive maintenance system of claim 1, wherein the one or more operations include at least one of the following operations of the one or more injection systems: a hardware operation of one or more hardware components, a mechanical operation, an electrical operation, a software operation of one or more software applications, a user interface operation, a communication operation, or any combination thereof.

3. The predictive maintenance system of claim 2, wherein the one or more operations include the hardware operation of the one or more hardware components, and wherein the one or more hardware components include at least one of the following hardware components of the one or more injection systems: a microprocessor, a memory, a storage component, an input component, an output component, a circuit board, a sensor, a pump, a valve, or any combination thereof.

4. The predictive maintenance system of claim 2, wherein the one or more operations include the mechanical operation, and wherein the mechanical operation includes providing the one or more fluids from the one or more fluid sources.

5. The predictive maintenance system of claim 1, wherein the one or more operation parameters include at least one of the following operation parameters associated with the one or more operations of the one or more injection systems: a mechanical force produced by the motor of the one or more injection systems; an achieved pressure; number of injections performed; a resistance; a current; a voltage; a noise or signal level; a movement above a threshold movement; power line conditions; an energy consumption; a duration of time powered-on; a linear amount of power delivered or used; a non-linear amount of power delivered or used; a flow rate during one or more injections; a difference between the flow rate during the one or more injections and a programmed flow rate of the one or more injections; a volume pumped and/or delivered during the one or more injections; a difference between the volume pumped and/or delivered during the one or more injections and a programmed volume to be pumped and/or to be delivered during the one or more injections; a duration of time of the one or more injections; a pressure limit or threshold beyond which the one or more injection systems are programmed to cease delivery of the one or more injections; a temperature and/or a humidity within the one or more injection systems; a number of times power has been cycled; a number, a duration and/or a type of user interface keys actuated; an existence or operability of communications with one or more other systems or devices; a number and/or a type of error codes received; a number of scans performed by one or more image capture devices before a successful scan of at least one bar code; a number of one or more disposables sold to and/or used by an associated customer; a type of contrast used; a temperature over one or more time periods within the one or more injection systems; a temperature and/or a humidity of an environment surrounding the one or more injection systems; an indication of liquid within the one or more injection systems; an identifier of a user or operator; a staff rating of wear; a staff rating of cleanliness; or any combination thereof.

6. The predictive maintenance system of claim 5, wherein the one or more operation parameters include the mechanical force produced by the motor, and wherein the predictive maintenance system further comprises:

one or more force sensors configured to measure the mechanical force produced by the motor to provide the one or more fluids from the one or more fluid sources, wherein the one or more prediction scores include one or more predictions of one or more operation failures or misuses for the one or more injection systems associated with a build-up of wear, contrast and/or dirt in connection therewith such that an effect of the build-up of wear, contrast and/or dirt for each of the one or more injection systems is determined by a comparison of the force of the motor thereof for a current or more recent injection operation to the force of the motor thereof for one of previous injection operations and a calibration operation of the motor.

7. The predictive maintenance system of claim 5, wherein the one or more operation parameters include the flow rate during the one or more injections and the volume pumped and/or delivered during the one or more injections, and wherein the one or more prediction scores include one or more predictions of one or more operation failures or misuses for the one or more injection systems associated with a build-up of wear, contrast and/or dirt in connection therewith such that an effect of the build-up of wear, contrast and/or dirt for each of the one or more injection systems is determined by applying at least one of a cube root life equation and one or more other suitable equations to the flow rate during the one or more injections and the volume pumped and/or delivered during the one or more injections, wherein a maximum achieved pressure is substituted for an average load and the flow rate during the one or more injections and the volume pumped and/or delivered during the one or more injections establishes a duration of a load to determine the one or more prediction scores.

8. The predictive maintenance system of claim 5, wherein the one or more operation parameters include the number of scans performed by the one or more image capture devices before the successful scan of the at least one bar code, and wherein the predictive maintenance system further comprises:

the one or more image capture devices configured to read at least one barcode.

9. The predictive maintenance system of claim 8, wherein the one or more image capture devices are positioned on or recessed in a housing of the injector or within at least a portion of an inner surface of at least one syringe port of the injector.

10. The predictive maintenance system of claim 1, further comprising:

one or more image capture devices positioned to have a field of view that includes one or more components of the one or more injection systems for capturing one or more images of the one or more components of the one or more injection systems, wherein the at least one processor is further programmed and/or configured to:

analyze the one or more images using one or more image processing techniques to identify at least one of (i) a percentage of the one or more components that are covered in unwanted contaminants and (ii) a leak or a crack in the one or more components, wherein the one or more prediction scores include one or more predictions of one or more operation failures or misuses for the one or more injection systems associated with new or increased contaminant coverage thereon and/or a leak or a crack in the one or more components determined by a comparison of current images to training images or previous images to identify the new or increased contaminant coverage and/or the leak or the crack in the one or more components.

11. The predictive maintenance system of claim 1, wherein the maintenance data includes a prompt to a user to initiate at least one maintenance action associated with the one or more injection systems.

12. The predictive maintenance system of claim 11, wherein the at least one maintenance action includes at least one of the following maintenance actions: scheduling a service for the one or more injection systems; operating the one or more injection systems in a specific manner indicated by the maintenance data; requesting a service directly from the one or more injection systems; or any combination thereof.

13. The predictive maintenance system of claim 1, wherein the maintenance data includes an instruction to the one or more injection systems that causes the one or more injection systems to automatically initiate at least one maintenance action.

14. The predictive maintenance system of claim 13, wherein the at least one maintenance action includes at least one of the following: prompt to a user to initiate at least one maintenance action associated with the one or more injection systems; transmitting operation data and/or an alert to a remote system; providing remote entry to a remote computing system to modify and/or update software and/or the one or more operation parameters; scheduling a service technician; performing a specific operation; providing a recommendation to improve service based on a comparison of the one or more injection systems to one or more other injection systems; rebooting software of the one or more injection systems; updating the software of the one or more injection systems; offering a customized preventative maintenance service; offering a service plan based on usage-based operation parameters; disabling or limiting one or more operations or functions; cycling power, disabling power; recommending training to a user; measuring component degradation, wear, or cleanliness; providing instructions to use the one or more injection systems in a specific manner to avoid a specific operation failure and/or misuse; placing an order for one or more disposables and/or one or more contrast agents; or any combination thereof.

15. The predictive maintenance system of claim 1, further comprising:
one or more sensors configured to measure the one or more operation parameters associated with the one or more operations of the one or more injection systems, wherein the one or more sensors include at least one of the following sensors: a flow rate sensor; a temperature sensor; an accelerometer; a strain gauge; a motor current sensor; an image sensor; an air sensor; a force sensor; or any combination thereof.

16. The predictive maintenance system of claim 1, wherein the one or more operation failures or misuses for the one or more injection systems include at least one of the following: failure of an electrical component, failure of a software component, failure of a mechanical component, receiving, with the one or more injection systems, of user input from a user of the one or more injection systems that causes the one or more injection systems to operate contrary to one or more predefined operation thresholds, or any combination thereof.

17. A computer program product for predictive maintenance, the computer program product comprising at least one non-transitory computer-readable medium including program instructions that, when executed by at least one processor, cause the at least one processor to:
control one or more vibration monitoring sensors to measure a vibration frequency and/or amplitude of the injector motor of the injector during one of: (i) moving, with a motor, a plunger via a respective piston element to deliver fluid from a syringe of an injector and (ii) powering, with the motor, a pump to pump fluids from a fluid source of the injector, for the one or more injection systems for one or more injection operations;
receive operation data associated with the one or more injection systems, wherein the operation data includes one or more operation parameters associated with one or more operations of the one or more injection systems, and wherein the one or more operation parameters include for each of the one or more injection systems the vibration frequency and/or amplitude of the injector motor thereof measured by the one or more vibration monitoring sensors for the one or more injection operations;
determine one or more prediction scores for the one or more injection systems based on the operation data including for each of the one or more injection systems the vibration frequency and/or amplitude of the injector motor thereof measured by the one or more vibration monitoring sensors for the one or more injection operations, wherein the one or more prediction scores include one or more predictions of one or more operation failures or misuses for the one or more injection systems associated with a build-up of wear, contrast, and/or dirt in connection therewith, such that an effect of the build-up of wear, contrast, and/or dirt for each of the one or more injection systems is determined by applying a pattern prediction model to the vibration frequency and/or amplitude of the injector motor thereof measured by the one or more vibration monitoring sensors;
provide maintenance data associated with the one or more operation failures or misuses, wherein the maintenance data is determined based on the one or more prediction scores, wherein the maintenance data includes a prediction of a remaining time of use and/or a remaining number of uses for the one or more injection systems until one or more operation failures or misuses for the one or more injection systems associated with a build-up of wear, contrast, and/or dirt in connection therewith; and
automatically disable, based on the maintenance data, the one or more injection systems from performing an injection operation.

18. An injection system, comprising:
an injector including a motor configured to one of: (i) move a plunger via a respective piston element to deliver fluid from a syringe of the injector and (ii) power a pump to pump fluids from a fluid source of the injector;
one or more vibration monitoring sensors configured to measure a vibration frequency and/or amplitude of the injector motor of the injector during one of: (i) moving, with the motor, the plunger to deliver fluid from the syringe of the injector and (ii) powering, with the motor, the pump to pump fluids from the fluid source of the injector, for the injection system for one or more injection operations;
a computer system comprising one or more processors programmed or configured to:
receive operation data associated with the injector, wherein the operation data includes one or more operation parameters associated with the one or more operations of the injector, and wherein the one or more operation parameters include the vibration frequency and/or amplitude of the injector motor thereof measured by the one or more vibration monitoring sensors for the one or more injection operations;
determine one or more prediction scores for the injector based on the operation data including the vibration frequency and/or amplitude of the injector motor thereof measured by the one or more vibration monitoring sensors for the one or more injection operations, wherein the one or more prediction scores include one or more predictions of one or more operation failures or misuses for the injector associated with a build-up of wear, contrast, and/or dirt in the injector, such that an effect of the build-up of wear, contrast, and/or dirt for the injector is determined by applying a pattern prediction model to the vibration frequency and/or amplitude of the injector motor thereof measured by the one or more vibration monitoring sensors;
provide maintenance data associated with the one or more operation failures or misuses, wherein the maintenance data is determined based on the one or more prediction scores, wherein the maintenance data includes a prediction of a remaining time of use and/or a remaining number of uses for the injection system until one or more operation failures or misuses for the injection system associated with a build-up of wear, contrast, and/or dirt in connection therewith; and
automatically disable, based on the maintenance data, the one or more injection systems from performing an injection operation.

19. The injection system of claim 18, wherein the one or more operations include at least one of the following operations: a hardware operation of one or more hardware components, a mechanical operation, an electrical operation, a software operation of one or more software applications, a user interface operation, a communication operation, or any combination thereof.

20. The injection system of claim 19, wherein the one or more operations include the hardware operation of the one or more hardware components, and wherein the one or more hardware components include at least one of the following hardware components: a microprocessor, a memory, a storage component, an input component, an output component, a circuit board, a sensor, a pump, a valve, or any combination thereof.

21. The injection system of claim 19, wherein the one or more operations include the mechanical operation, and wherein the mechanical operation includes providing the one or more fluids from the one or more fluid sources.

22. The injection system of claim 18, wherein the one or more operation parameters include at least one of the following operation parameters associated with the one or more operations of the injector: a mechanical force produced by the motor of the injection system; an achieved pressure; number of injections performed; a resistance; a current; a voltage; a noise or signal level; a movement above a threshold movement; power line conditions; an energy consumption; a duration of time powered-on; a linear amount of power delivered or used; a non-linear amount of power delivered or used; a flow rate during one or more injections; a difference between the flow rate during the one or more injections and a programmed flow rate of the one or more injections; a volume pumped and/or delivered during the one or more injections; a difference between the volume pumped and/or delivered during the one or more injections and a programmed volume to be pumped and/or to be delivered during the one or more injections; a duration of time of the one or more injections; a pressure limit or threshold beyond which the injection system is programmed to cease delivery of the one or more injections; a temperature and/or a humidity within the injection system; a number of times power has been cycled; a number, a duration and/or a type of user interface keys actuated; an existence or operability of communications with one or more other systems or devices; a number and/or a type of error codes received; a number of scans performed by one or more image capture devices before a successful scan of at least one bar code; a number of one or more disposables sold to and/or used by an associated customer; a type of contrast used; a temperature over one or more time periods within the injection system; a temperature and/or a humidity of an environment surrounding the injection system; an indication of liquid within the injection system; an identifier of a user or operator; a staff rating of wear; a staff rating of cleanliness; or any combination thereof.

23. The injection system of claim 22, wherein the one or more operation parameters include the mechanical force produced by the motor, and wherein the injection system further comprises:
one or more force sensors configured to measure the mechanical force produced by the motor to provide the one or more fluids from the one or more fluid sources, wherein the one or more prediction scores include one or more predictions of one or more operation failures or misuses for the injection system associated with a build-up of wear, contrast and/or dirt in connection therewith such that an effect of the build-up of wear, contrast and/or dirt for the injection system is determined by a comparison of the force of the motor thereof for a current or more recent injection operation to the force of the motor thereof for one of previous injection operations and a calibration operation of the motor.

24. The injection system of claim 22, wherein the one or more operation parameters include the flow rate during the one or more injections and the volume pumped and/or delivered during the one or more injections, and wherein the one or more prediction scores include one or more predictions of one or more operation failures or misuses for the injection system associated with a build-up of wear, contrast and/or dirt in connection therewith such that an effect of the build-up of wear, contrast and/or dirt for the injection system is determined by applying at least one of a cube root life equation and one or more other suitable equations to the flow rate during the one or more injections and the volume pumped and/or delivered during the one or more injections, wherein a maximum achieved pressure is substituted for an average load and the flow rate during the one or more injections and the volume pumped and/or delivered during the one or more injections establishes a duration of a load to determine the one or more prediction scores.

25. The injection system of claim 22, wherein the one or more operation parameters include the number of scans performed by the one or more image capture devices before the successful scan of the at least one bar code, and wherein the injection system further comprises:

the one or more image capture devices configured to read at least one barcode.

26. The injection system of claim 25, wherein the one or more image capture devices are positioned on or recessed in a housing of the injector or within at least a portion of an inner surface of at least one syringe port of the injector.

27. The injection system of claim 18, further comprising:
one or more image capture devices positioned to have a field of view that includes one or more components of the injection system for capturing one or more images of the one or more components of the injection system, wherein the at least one processor is further programmed and/or configured to:
analyze the one or more images using one or more image processing techniques to identify at least one of (i) a percentage of the one or more components that are covered in unwanted contaminants and (ii) a leak or a crack in the one or more components, wherein the one or more prediction scores include one or more predictions of one or more operation failures or misuses for the injection system associated with new or increased contaminant coverage thereon and/or a leak or a crack in the one or more components determined by a comparison of current images to training images or previous images to identify the new or increased contaminant coverage and/or the leak or the crack in the one or more components.

28. The injection system of claim 18, wherein the maintenance data includes a prompt to a user to initiate at least one maintenance action associated with the injection system.

29. The injection system of claim 28, wherein the at least one maintenance action includes at least one of the following maintenance actions: scheduling a service for the injection system; operating the injection system in a specific manner indicated by the maintenance data; requesting a service directly from the injection system; or any combination thereof.

30. The injection system of claim 18, wherein the maintenance data includes an instruction to the injection system that causes the injection system to automatically initiate at least one maintenance action.

31. The injection system of claim 30, wherein the at least one maintenance action includes at least one of the following: prompt to a user to initiate at least one maintenance action associated with the injection system; transmitting operation data and/or an alert to a remote system; providing remote entry to a remote computing system to modify and/or update software and/or the one or more operation parameters; scheduling a service technician; performing a specific operation; providing a recommendation to improve service based on a comparison of the injection system to one or more other injection systems; rebooting software of the injection system; updating the software of the injection system; offering a customized preventative maintenance service; offering a service plan based on usage-based operation parameters; disabling or limiting one or more operations or functions; cycling power, disabling power; recommending training to a user; measuring component degradation, wear, or cleanliness; providing instructions to use the injection system in a specific manner to avoid a specific operation failure and/or misuse; placing an order for one or more disposables and/or one or more contrast agents; or any combination thereof.

32. The injection system of claim 18, further comprising:
one or more sensors configured to measure the one or more operation parameters associated with the one or more operations of the injector, wherein the one or more sensors include at least one of the following sensors: a flow rate sensor; a temperature sensor; an accelerometer; a strain gauge; a motor current sensor; an image sensor; an air sensor; a force sensor; or any combination thereof.

33. The injection system of claim 18, wherein the one or more operation failures or misuses for the injection system include at least one of the following: failure of an electrical component, failure of a software component, failure of a mechanical component, receiving, with the injection system, of user input from a user of the injection system that causes the injection system to operate contrary to one or more predefined operation thresholds, or any combination thereof.

* * * * *

UNITED STATES PATENT AND TRADEMARK OFFICE
CERTIFICATE OF CORRECTION

PATENT NO. : 12,205,715 B2
APPLICATION NO. : 17/581648
DATED : January 21, 2025
INVENTOR(S) : Schriver et al.

Page 1 of 1

It is certified that error appears in the above-identified patent and that said Letters Patent is hereby corrected as shown below:

On the Title Page

Item (57), under "ABSTRACT", in Column 2, Line 6, delete "systems:" and insert -- systems; --, therefor.
On Page 2, item (56), under "OTHER PUBLICATIONS", in Column 2, Line 11, delete "Plublishing," and insert -- Publishing, --, therefor.

In the Specification

In Column 3, Line 60, delete "systems:" and insert -- systems; --, therefor.
In Column 7, Line 11, delete "one,"" and insert -- one." --, therefor.
In Column 9, Line 4, delete "etc,)" and insert -- etc.) --, therefor.
In Column 10, Line 32, delete "etc,)." and insert -- etc.). --, therefor.
In Column 12, Line 31, delete "122," and insert -- 122. --, therefor.
In Column 12, Line 65, delete "etc,)," and insert -- etc.), --, therefor.
In Column 15, Line 4, delete "etc)" and insert -- etc.) --, therefor.
In Column 17, Line 17, delete "eta)" and insert -- etc.) --, therefor.
In Column 20, Line 40, delete "etc.)," and insert -- etc.). --, therefor.
In Column 23, Line 40, delete "etc)," and insert -- etc.), --, therefor.
In Column 24, Line 16, delete "etc,)" and insert -- etc.) --, therefor.
In Column 24, Line 25, delete "etc.)," and insert -- etc.). --, therefor.
In Column 28, Line 19, delete "aspect," and insert -- aspect. --, therefor.

Signed and Sealed this
Tenth Day of June, 2025

Coke Morgan Stewart
*Acting Director of the United States Patent and Trademark Office*